United States Patent
Knudson et al.

(10) Patent No.: US 10,451,588 B2
(45) Date of Patent: *Oct. 22, 2019

(54) MAGNETO-MECHANICAL RESONATOR SENSOR WITH MASS DISTRIBUTION CHANNEL

(71) Applicant: 3M INNOVATIVE PROPERTIES COMPANY, St. Paul, MN (US)

(72) Inventors: Orlin B. Knudson, Vadnais Heights, MN (US); Jia Hu, Mounds View, MN (US); Chaodi Li, Woodbury, MN (US); Richard L. Rylander, Stillwater, MN (US); Cheryl Lee Senger Elsbernd, Woodbury, MN (US); Stephen J. Willett, St. Paul, MN (US); Andrew P. Bonifas, Alberta (CA)

(73) Assignee: 3M INNOVATIVE PROPERTIES COMPANY, St. Paul, MN (US)

(*) Notice: Subject to any disclaimer, the term of this patent is extended or adjusted under 35 U.S.C. 154(b) by 160 days.

This patent is subject to a terminal disclaimer.

(21) Appl. No.: 15/504,244

(22) PCT Filed: Aug. 25, 2015

(86) PCT No.: PCT/US2015/046673
§ 371 (c)(1),
(2) Date: Feb. 15, 2017

(87) PCT Pub. No.: WO2016/033029
PCT Pub. Date: Mar. 3, 2016

(65) Prior Publication Data
US 2017/0276647 A1    Sep. 28, 2017

Related U.S. Application Data

(60) Provisional application No. 62/042,362, filed on Aug. 27, 2014.

(51) Int. Cl.
*G01N 29/24* (2006.01)
*A61L 2/28* (2006.01)
(Continued)

(52) U.S. Cl.
CPC .......... *G01N 29/2412* (2013.01); *A61L 2/28* (2013.01); *G01K 3/04* (2013.01); *G01K 7/32* (2013.01);
(Continued)

(58) Field of Classification Search
CPC .. G01N 19/10; G01N 29/2412; G01N 27/026; G01N 29/036; G01N 2291/0256;
(Continued)

(56) References Cited

U.S. PATENT DOCUMENTS 4,801,862 A * 1/1989 Osaki ................. G01N 22/00
    324/631
4,850,716 A    7/1989 Baker
(Continued)

FOREIGN PATENT DOCUMENTS

WO    WO 2011-106825    9/2011
WO    WO 2016-032787    3/2016
(Continued)

OTHER PUBLICATIONS

Fabian, "Electronic tagging of Surgical sponges to prevent their accidental retention", Surgery, Mar. 2005, vol. 137, No. 3, pp. 298-301.
(Continued)

*Primary Examiner* — Lisa M Caputo
*Assistant Examiner* — Philip L Cotey
(74) *Attorney, Agent, or Firm* — X. Christina Huang

(57) ABSTRACT

Magneto-Mechanical Resonator Sensor with Mass Distribution Channel Some aspects of the present disclosure feature a sensing device (e.g. for temperature, moisture or
(Continued)

detection of substances) comprising a magnetic bias layer, a resonator, a spacer, and an environmental change receptor. The spacer is disposed between the magnetic bias layer and the resonator. At least one of the resonator surfaces has a predefined channel. The environmental change receptor is disposed proximate to the predefined channel. In response to a change in environment, the environmental change receptor distributes along a part of the channel.

20 Claims, 25 Drawing Sheets

(51) Int. Cl.
G01K 3/04 (2006.01)
G01K 7/32 (2006.01)
G01K 7/36 (2006.01)
G01K 11/06 (2006.01)
G01N 29/036 (2006.01)
G01N 27/02 (2006.01)

(52) U.S. Cl.
CPC ............ *G01K 7/36* (2013.01); *G01K 11/06* (2013.01); *G01N 27/026* (2013.01); *G01N 29/036* (2013.01); *G01N 2291/0256* (2013.01); *G01N 2291/02863* (2013.01)

(58) Field of Classification Search
CPC .. G01N 2291/02863; G01K 7/32; G01K 7/36; G01K 11/06; G01K 3/04; A61L 2/28
See application file for complete search history.

(56) References Cited

U.S. PATENT DOCUMENTS

| | | | |
|---|---|---|---|
| 5,334,941 A * | 8/1994 | King | G01N 22/00 324/637 |
| 5,716,681 A | 2/1998 | Williams | |
| 5,745,039 A * | 4/1998 | Hof | A61L 2/28 116/204 |
| 5,771,328 A | 6/1998 | Wortman | |
| 6,067,016 A | 5/2000 | Deschenes | |
| 6,218,944 B1 | 4/2001 | Kiesewetter | |
| 6,359,444 B1 | 3/2002 | Grimes | |
| 6,393,921 B1 | 5/2002 | Grimes | |
| 6,397,661 B1 * | 6/2002 | Grimes | G01K 7/38 324/207.13 |
| 6,534,319 B1 | 3/2003 | Liu | |
| 6,639,402 B2 | 10/2003 | Grimes | |
| 6,688,162 B2 | 2/2004 | Bachas | |
| 6,720,877 B2 | 4/2004 | Lian | |
| 6,752,837 B2 * | 6/2004 | Karp | G08B 13/2402 235/383 |
| 6,820,469 B1 * | 11/2004 | Adkins | G01H 13/00 73/24.06 |
| 7,176,344 B2 | 2/2007 | Gustafson | |
| 8,558,052 B2 * | 10/2013 | Nedestam | A61F 13/42 604/361 |
| 2002/0166382 A1 | 11/2002 | Bachas | |
| 2004/0113801 A1 | 6/2004 | Gustafson | |
| 2009/0302498 A1 | 12/2009 | Nedestam | |
| 2011/0033694 A1 | 2/2011 | Jing | |
| 2011/0312004 A1 | 12/2011 | Chinnayelka | |
| 2012/0068823 A1 | 3/2012 | Doany | |
| 2013/0099790 A1 | 4/2013 | Doany | |
| 2013/0291657 A1 * | 11/2013 | Purekar | G01L 3/101 73/862.333 |

FOREIGN PATENT DOCUMENTS

WO  WO 2016-032796  3/2016
WO  WO 2016-033026  3/2016

OTHER PUBLICATIONS

Grimes, "Environmental Monitoring Using Magnetoelastic Sensors (Invited Paper)", Proceedings of SPIE, 2000, vol. 4097, pp. 123-133.
Grimes, "Magnetoelastic sensors for remote query environmental monitoring", Smart Mater. Struct. 1999, vol. 8, pp. 639-646.
Grimes, "Wireless Magnetoelastic Resonance Sensors: A Critical Review", Sensors, 2002, vol. 2, pp. 294-313. XP002710067.
Jain, "Magnetoacoustic Remote Query Temperature and Humidity Sensors", Smart Mater. Struct., 2000, vol. 9, pp. 502-510.
Lebras, "A new magnetoelastic resonance based technique to determine magnetomechanical parameters of amorphous ferromagnetic ribbons", Review of Scientific Instruments, 2013, vol. 84, pp. 1-17.
Ong, "Magnetism-based Sensors", Proceedings of SPIE, 2001, vol. 4467, pp. 158-172.
International Search Report for PCT International Application No. PCT/US2015/046673 dated Nov. 11, 2015, 5 pages.

* cited by examiner

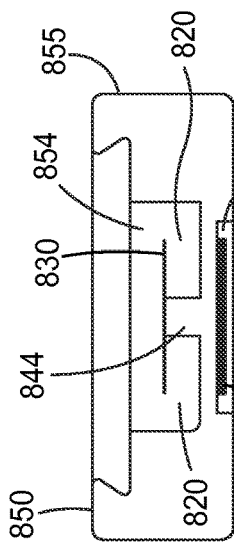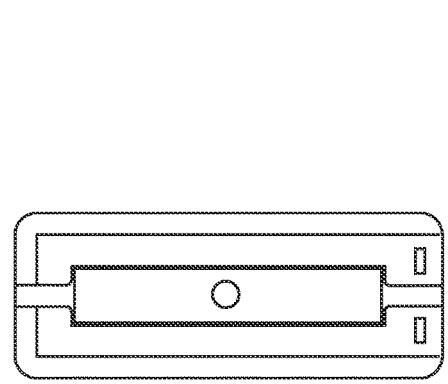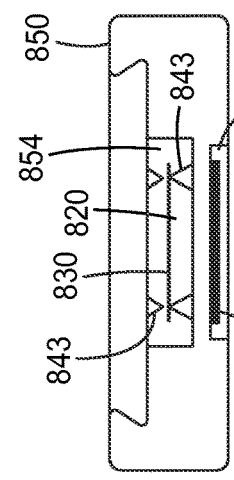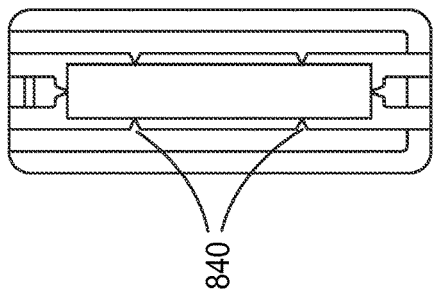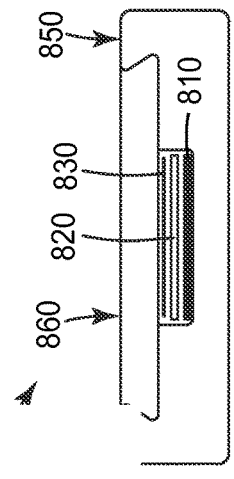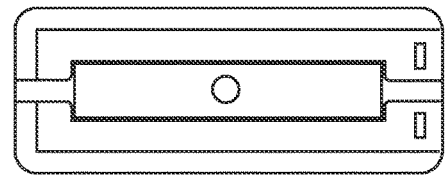

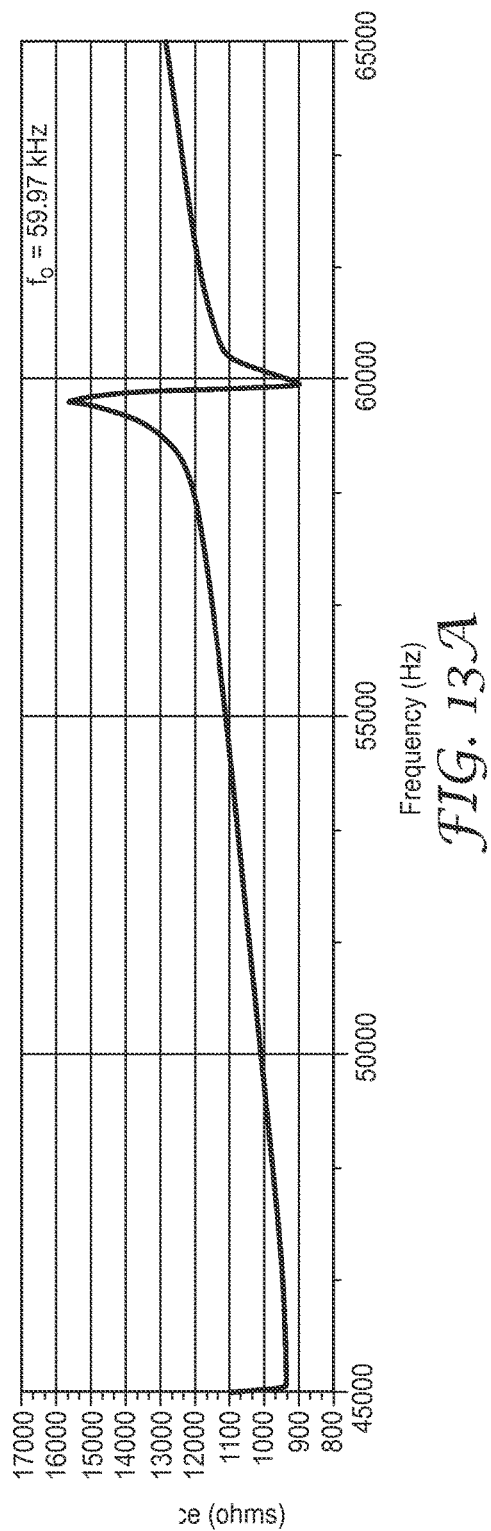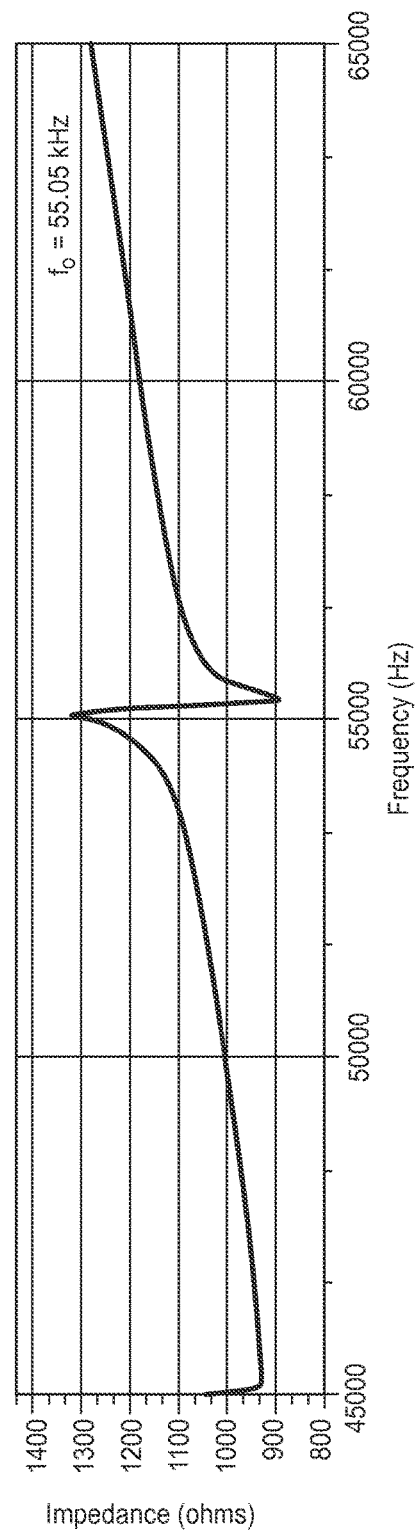
FIG. 13A
FIG. 13B

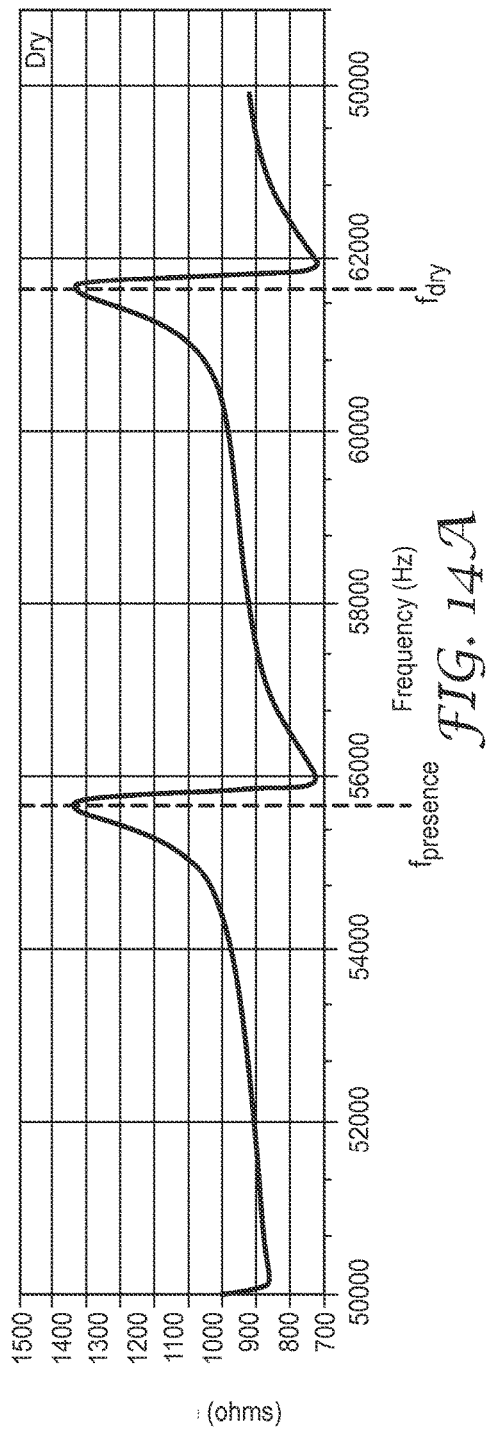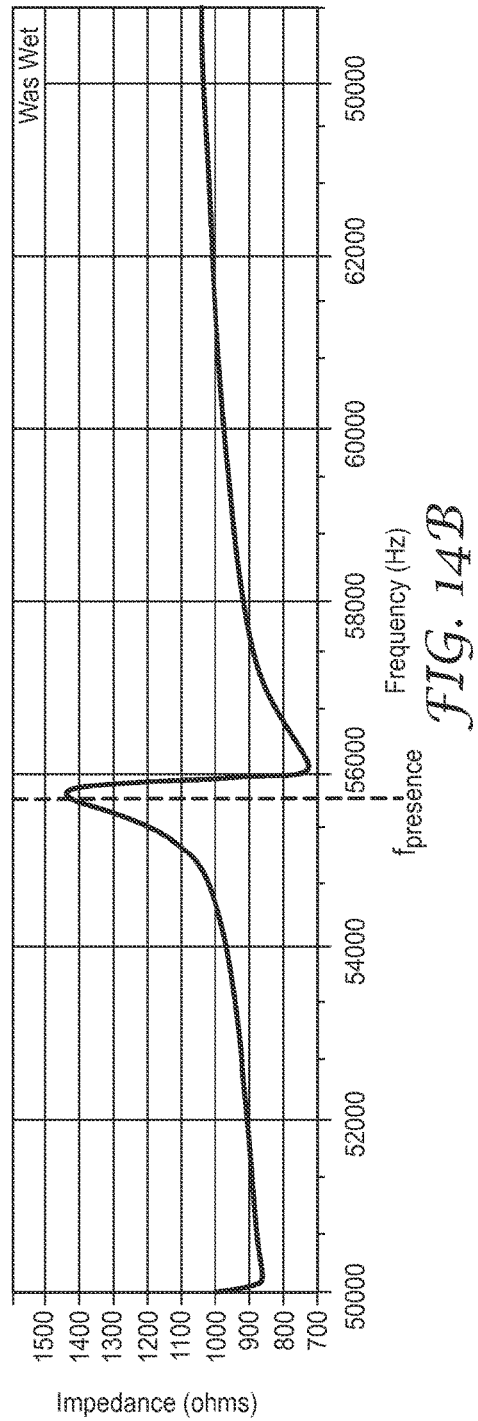

MAGNETO-MECHANICAL RESONATOR SENSOR WITH MASS DISTRIBUTION CHANNEL

CROSS REFERENCE TO RELATED APPLICATIONS

This is a national stage filing under 35 U.S.C. 371 of PCT/US2015/046673, filed on Aug. 25, 2015, which claims priority to U.S. provisional Application No. 62/042362, filed on Aug. 27, 2014, the disclosure of which are incorporated by reference in their entirety herein.

TECHNICAL FIELD

The present disclosure relates to magneto-mechanical resonator sensors designed to monitor environmental and biological variables and the systems using these sensors.

BACKGROUND

Magneto-mechanical resonators (MMR) are energized using a radio frequency source that generates a magnetic field. MMR sensors are based on the principles of magnetostriction and magneto-elastic coupling. Magnetostriction involves changing the shape of a ferromagnetic material when subjected to a magnetic field. Magneto-elastic coupling involves the relationship among the stress and strain of a material when subjected to a magnetic field.

Typically, a MMR sensor is coupled to an external magnetic field and receives magnetic energy from the magnetic field. The MMR sensor converts magnetic energy to mechanical oscillations. When the magnetic field is removed, the mechanical oscillations are converted to magnetic energy and the sensor radiates a magnetic field at a resonant frequency. A detector can then measure the radiated magnetic energy from the sensor. MMR can be used to construct wireless sensors to monitor environmental and biological variables.

SUMMARY

Some aspects of the present disclosure feature a sensing device comprising a magnetic bias layer, a resonator, a spacer, and an environmental change receptor. The magnetic bias layer has a first magnetic surface and an opposing second magnetic surface and the magnetic bias layer has a first magnetic material. The resonator has a first resonator major surface and an opposing second resonator major surface. The resonator uses a second magnetic material. The second resonator major surface is facing toward the first magnetic surface. The first resonator major surface has a predefined channel. The spacer is disposed between the magnetic bias layer and the resonator. The environmental change receptor is disposed proximate to the predefined channel.

In one example, a sensing device comprises a magnetic bias layer, a resonator, a spacer, an environmental change receptor and a housing. The magnetic bias layer has a first magnetic surface and an opposing second magnetic surface. The magnetic bias layer comprises a first magnetic material. The resonator has a first resonator major surface and an opposing second resonator major surface. The resonator comprises a second magnetic material. The second resonator major surface is facing toward the first magnetic surface. The first resonator major surface has a predefined channel. The spacer is disposed between the magnetic bias layer and the resonator. The environmental change receptor is disposed proximate to the predefined channel. The housing has one or more openings and contains the magnetic bias layer, the resonator, and the spacer.

In another example, a sensing device comprises a magnetic bias layer, a resonator, a spacer, an environmental change receptor and a housing. The magnetic bias layer has a first magnetic surface and an opposing second magnetic surface. The magnetic bias layer comprises a first magnetic material. The resonator has a first resonator major surface and an opposing second resonator major surface. The resonator comprises a second magnetic material. The second resonator major surface is facing toward the first magnetic surface. The first resonator major surface has a predefined channel. The spacer is disposed between the magnetic bias layer and the resonator. The environmental change receptor is disposed proximate to the predefined channel. The housing contains the magnetic bias layer, the resonator, and a supporting structure to support the resonator.

BRIEF DESCRIPTION OF DRAWINGS

The accompanying drawings are incorporated in and constitute a part of this specification and, together with the description, explain the advantages and principles of the invention. In the drawings.

FIGS. 8A-8H illustrate some examples of MMR sensors with different housing constructions;

FIGS. 13A-13D are impedance versus frequency graphs of example embodiments of MMR sensors used for sterilization monitoring with different configurations;

FIGS. 14A-14B are impedance versus frequency graphs of example embodiments of MMR sensors used for wetness monitoring with different configurations.

DETAILED DESCRIPTION

Figure 1A:
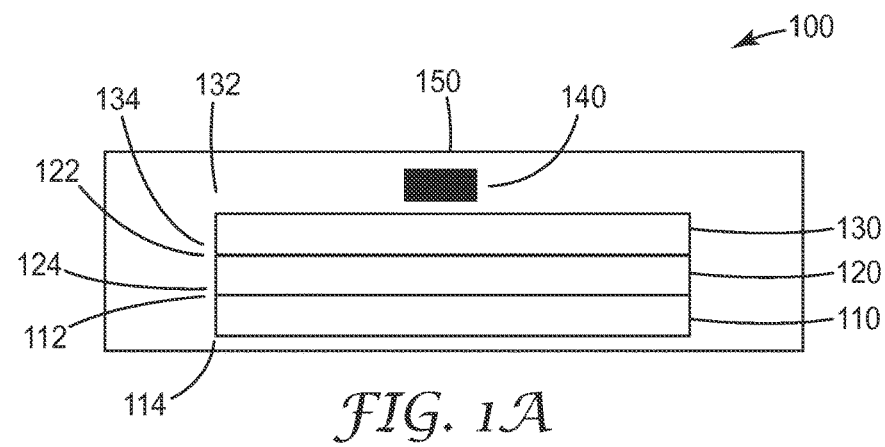
FIG. 1A is a side view of one embodiment of an MMR sensor.

MMR sensors can be used to monitor environmental variables including, but not limited to, temperature, moisture, the presence or absence of biological, physical and/or chemical substance, or any combination thereof. MMR sensors can also be used to monitor or measure the variance of environmental variables over time. Typically, one or more MMR sensors disposed in the environment experience mass and/or elastic modulus changes on a magneto-elastic strip (i.e., resonator) in response to changes to and/or in environmental variables. The mass changes can include changes in amount of materials and/or distribution of materials disposed on the resonator. A mass change can produce a detectable frequency shift of the resonant frequency of the corresponding MMR sensors. A measurement device can be used to measure the frequency shift and the measurement can be used to evaluate or determine the change of the environmental variable.

At least some aspects of the present disclosure are directed to designs and constructions of MMR sensors that experience frequency shifts in response to environmental changes. In some embodiments, a MMR sensor is constructed in a way that an environmentally responsive material is designed to distribute along a specific path or pattern on a magneto-elastic strip of the MMR sensor in response to environmental changes. The specific path or pattern is selected to allow the MMR sensor to generate an amplified signal of frequency shift greater than that of the frequency shift of the mass being distributed uniformly or uncontrolled. In some other embodiments, an environmentally responsive material is predisposed on a magneto-elastic strip of the MMR sensor and the mass of the environmentally responsive material is changed or the disposition is changed in response to environmental changes. In some cases, the environmentally responsive material is predisposed at one or more specific portions of the magneto-elastic strip, for example, proximate to one end of the strip. In some other cases, the environmentally responsive material is predisposed along a specific path or according to a specific pattern on the magneto-elastic strip. In some embodiments, a MMR sensor is constructed to include an environmentally responsive material that will expand in response to environmental changes and thereby cause detectable changes to the oscillation of the resonator.

At least some aspects of the present disclosure are directed to systems and methods of detecting environmental changes using MMR sensors. In some embodiments, a sensing system can include a measurement device to monitor the frequency shifts of the MMR sensors. For example, the measurement device can be a gated oscillator including coil that produces a brief sinusoidal pulse at the resonant frequency, which is magnetically coupled to the MMR sensor and energizes the sensor. At the end of the energizing pulse, the coil is used as a receiver to monitor the decaying oscillations of the MMR sensor. As another example, the measurement device can make use of the mechanical vibration of the sensor where an oscillating magnetic field is partially converted to acoustic energy. The sound produced by the sensor is then detected by a microphone with appropriate frequency response. An advantage of acoustic method is that the sensor can be measured while it is being energized.

Figure 1B:
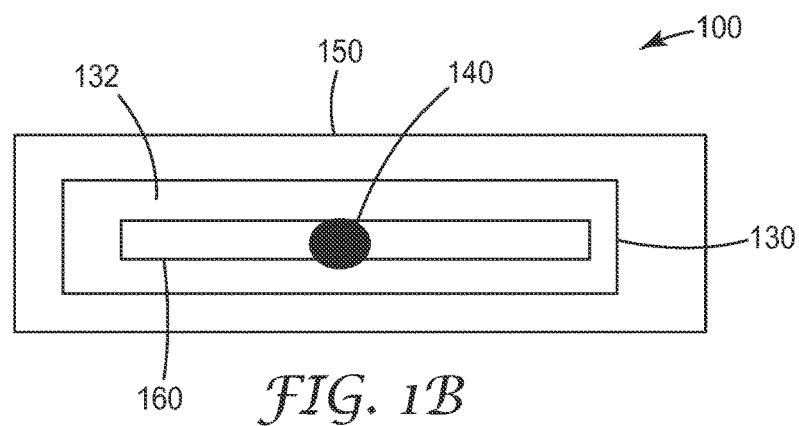
FIG. 1B is a top plane view of the MMR sensor illustrated in FIG. 1A with cover lifted.
Figure 1C:
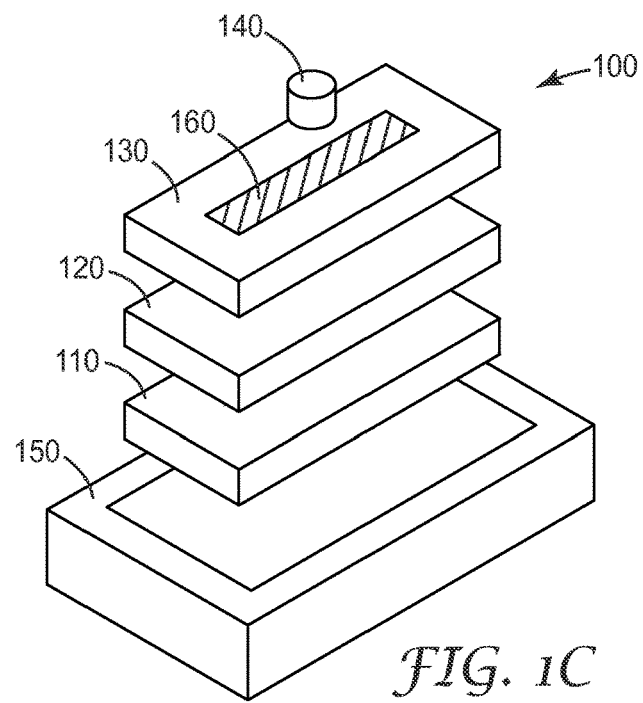
FIG. 1C is an exploded view of the MMR sensor illustrated in FIG. 1A.

FIG. 1A is a side view of one embodiment of an MMR sensor 100. FIG. 1B is a top plane view of the MMR sensor 100 with cover lifted and FIG. 1C is an exploded view of the MMR sensor 100. In the embodiment illustrated, the sensor 100 includes a magnetic bias layer 110, a spacer 120, a resonator 130, an environmental change receptor 140, and an optional housing 150. The magnetic bias layer 110, the spacer 120, the resonator 130, and the environmental change receptor 140 are contained in the housing 150.

The environmental change receptor 140 can include one or more environmentally responsive or sensitive materials selected depending on the sensing needs. The environmentally responsive material can be selected based on its solubility, boiling point, melting point, ability to absorb gases or liquids, promote bacterial growth, softening point or flow properties, such that it changes properties (evaporates or redistributes on the sensor strip) in response to specific environmental conditions. In some cases, the environmental change receptor 140 can include more than one part, where each part can include similar or different environmentally responsive materials, and be disposed at different locations.

In some embodiments to monitor or measure temperature, the environmental change receptor 140 can include a type of meltable or flowable material, for example, crystalline or semi-crystalline materials, thermoplastics, polymers, wax, organic compounds such as salicylamide, polyethylene-co-acrylic acid, sucrose and the like. In some cases, the environmentally responsive material is selected based on its response to combined conditions of temperature and humidity, or temperature, humidity and time. The material can be selected to tailor to a particular application. In some embodiments to monitor the presence of chemical substance, the environmental change receptor 140 can include a type of material absorbing or reacting with the chemical substance. In an example of detecting gas, the environmental change receptor 140 can include Zeolite HiSiv 3000 powder from UOP LLC, Des Plaines, Ill.

The magnetic bias layer 110 has a first magnetic surface 112 and an opposing second magnetic surface 114. The spacer 120 is disposed between the magnetic bias layer 110 and the resonator 130. The spacer 120 having a first spacer surface 122 and an opposing second spacer surface 124. The second spacer surface 124 is adjacent to the first magnetic surface 112. The resonator 130 has a first resonator major surface 132 and an opposing second resonator major surface 134. The second resonator major surface 134 is adjacent to the first spacer surface 122. In some embodiments, the first resonator major surface has a predefined channel 160. In some cases, the predefined channel 160 can be mechanically or chemically constructed. The environmental change receptor 140 is disposed proximate to the predefined channel 160. In some cases, the materials in the environmental change receptor 140 will distribute along the predefined channel 160 in response to environmental changes, such as heat, increased humidity, or the like.

The magnetic bias layer 110 and the resonator 130 are made from magnetic materials, also referred to as electromagnetic materials or ferromagnetic materials. For example, the magnetic bias layer 110 can use magnets or magnetically hard or semi-hard metals, for example, magnets from Arnold Magnetic Technologies headquartered in Rochester, N.Y. Magnetic bias layer 110 can be made from any magnetic material that has sufficient magnetic remanence when magnetized to appropriately bias the resonator 130, and sufficient magnetic coercivity so as not to be magnetically altered in normal operating conditions. For example, a commercially available magnetic material such as ArnoKrome™ III from The Arnold Engineering Company of Marengo, Ill., can be used for the magnetic bias layer 110. Magnetic bias layer 110 can have dimensions similar to those of resonator 130.

The resonator 130 can use alloy materials that have high magnetostrictive coupling coefficients and/or high magneto-elastic coupling coefficients. In some embodiments, the resonator 130 can use magnetic amorphous alloy or crystalline materials that have high magnetostrictive coupling coefficients and/or high magneto-elastic coupling coefficients, for example, Metglas™ 2826 MB, 2605SA1 or 2605S3A made by Metglas™ of Conway, S.C. In some cases, the resonator 130 uses electromagnetic materials that have a magnetostrictive coupling coefficient equal to or greater than 10E-5. Resonator 130 may include one or more single resonator pieces. The resonator 130 resonates at a frequency dependent primarily upon its length, the strength of the magnetic bias field, the materials density, and the materials Young's modulus. While a resonator 130 can physically be designed to resonate at a wide range of frequencies, it may be desirable to tune the resonator 130 to particular frequencies. For example, a resonator 130 may be designed to resonate at a target frequency in the range of about 25 kHz to 45 kHz or within the range of about 45 kHz to 75 kHz. In some embodiments, a resonator 130 can include multiple resonator pieces, where each resonator piece is designed to resonate at a similar or different target frequency. In such embodiments, each target frequency can be used to encode an environmental variable to be monitored. For example, the target frequencies could be separated by 4 kHz intervals, such as, 46 kHz, 50 kHz, 54, kHz, 58 kHz, 62 kHz, etc. Because of variations in manufacturing process and/or materials in resonators 130, for example, the detected frequency is usually within a range varied from the target frequency. For example, for a target frequency of 58 kHz, the detected frequency can be within the range of 57 kHz to 59 kHz.

The spacer 120 can include one or more dielectric materials. In some embodiments, the resonator 130 is separated from the magnetic bias layer 110 by a spacer 120 to allow it to move freely. In some cases, the spacer 120 has a proper thickness such that the spacer 120 and the magnetic bias layer 110 together can provide the resonator 130 about 5 Oersteds-9 Oersteds of magnetic field bias intensity. Thickness of spacers 120 can range from 2.54E-3 cm (0.001 inches) to 6.35E-1 cm (0.25 inches), for example, 1.52E-1 cm (0.06 inches). In some cases, the spacer 120 can be primarily air. In some other cases, the spacer can include polymeric films. Other example of the spacer 120 can be non-metallic material (e.g., polycarbonate). In some configurations, the spacer 120 can be an integrated part of the housing. For example, the spacer 120 can include a supporting structure of the housing to separate the resonator 130 from magnetic bias layer 110.

In some embodiments, the predefined channel 160 can include path(s) and/or pattern(s). In some implementations, the predefined channel 160 can be constructed via mechanical and/or chemical approaches. For example, the first major resonator surface 132 is treated with laser etching to generate the predefined channel 160. In another example, the predefined channel 160 is recessed from the first major resonator surface 132. In some embodiments, materials that absorb or wick, such as paper or string, may be used to generate the predefined channel 160. In some embodiments, the wicking material is adhered to the first major resonator surface 132 in a predefined channel. In some examples, the wicking material may be arranged in a specific pattern or configuration to permit or guide the flow of the environmental responsive material. In some embodiments, the predefined channel may be a polymeric film with a microreplicated surface structure or a microreplicated capillary structure. The microreplicated film used as the predefined channel may be adhered to the resonator surface with an adhesive. Some examples of microreplicated films are described in U.S. Pat. Nos. 5,716,681 and 5,771,328, which are incorporated by reference in their entireties. The peaks of the micrreplicated channels can have the height of, for example, 10 microns, 400 microns, or higher.

In some cases, the first major resonator surface 132 is treated to generate the predefined channel 160 to cause a preferential flow pattern. This can be achieved by chemically treating or coating the resonator in selected areas or in specific patterns to either favor or deter flow along a particular path. For example, coating the channel or pattern with materials which are compatible with or interact with the environmentally responsive material will favor flow along those areas. As another example, for environmentally responsive material in form of wax, the surface of the predefined channel can be made oleophilic to promote flow in the channel. In another example, mechanically durable sintered coatings such as nanosilica may be used to chemically create the predefined channel 160. Coating particles may be applied from an aqueous dispersion and subsequently sintered by the application of heat. An acid sintering method may also be used to create the predefined channel 160, as described in U.S. Patent Publication No. 20110033694, the entirety of which is incorporated herein by reference.

In some other cases, the first major resonator surface 132 is treated to generate the predefined channel 160 to cause environmentally responsive materials unlikely to flow in a certain manner. In these cases, flow might be inhibited in certain treated areas due to treatment with incompatible coatings relative to the environmentally responsive material. For example, the first major resonator surface may be treated around the perimeter of the surface with a treatment or coating that inhibits flow of the environmental responsive materials to the edges. In some embodiments, the first major resonator surface is treated with two different treatments, such that flow is favored in certain areas and not in others. In some embodiments, the chemical treatment or coating is selected based on the particular need for hydrophilic, hydrophobic, oleophilic or oleophobic channels in a given sensor application. For example, for environmentally responsive material in the form of wax, the surface can be made oleophobic to inhibit flow in the channel or around the perimeter.

The housing 150 may use rigid materials to provide sufficient room for resonator 130 to resonate or vibrate. The housing 150 may be plastic or any other non-conductive material. The housing may include supporting structure(s) or protrusions to constrain resonator 130 from moving away too much from the bias magnet 110, or to reduce the potential for friction or viscous interaction between resonator and housing, for example. Housing 150 can seal and secure magnetic bias layer 110, spacer 120, and resonator 130. Housing 150 can be secured by, for example, adhesive, heat sealing, ultrasonic welding, or the like. In some cases, the spacer 120 can be supporting structures of the housing 150 (e.g., protrusions) that define planes where various components rest. The housing 150 may have openings, vent(s), holes or permeable materials to allow the resonator to interact with external environment. Environmental elements that interact with resonator include, for example, air, water, vapor, liquid, gas, biological substance, chemical substance, spores, or the like.

Figure 1D:
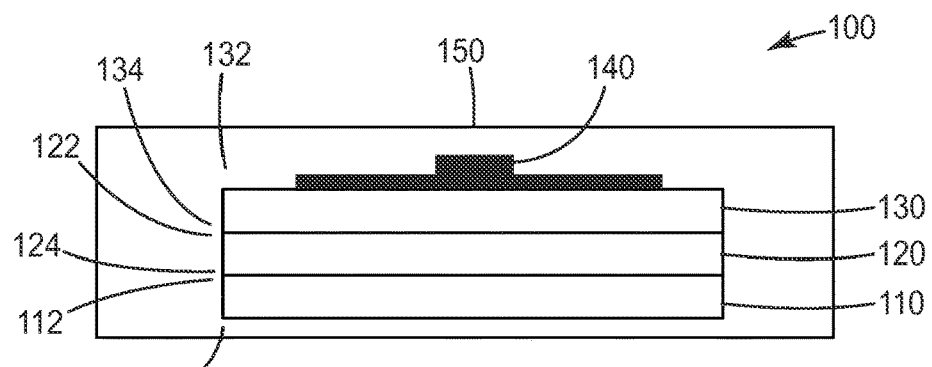
FIG. 1D is a side view illustrating an example of the MMR sensor illustrated in FIG. 1A after environment changes.
Figure 1E:
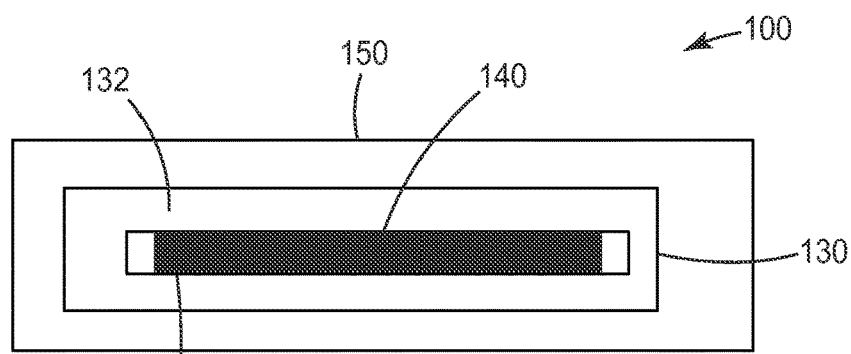
FIG. 1E is a top plane view of the example shown in FIG. 1D with cover lifted.

FIG. 1D is a side view illustrating an example of the MMR sensor 100 after environmental changes; and FIG. 1E is a top plane view of the example illustrated in FIG. 1D with cover lifted. The environmental change receptor 140 has changed its formation in response to changes to the environmental variables, such as the increase of temperature. As illustrated, the environmental change receptor 140 distributes along the predefined channel 160 attached to the first major resonator surface 132 of the resonator 130. The mass of the resonator 130 is changed because of such disposition of the environmental change receptor 140 on the resonator 130.

For a MMR sensor, the operation principle is to utilize a change of the resonant frequency as a result of changes to the mass of the resonator and/or the distribution of the mass on the resonator, for example, material binding, material removal, material flow. Usually, a thin magneto-elastic strip (i.e., resonator) is used in the sensor construction. The first order resonant frequency $f_0$ in the longitudinal mode at a freestanding strip is:

$$f_0 = \frac{1}{2L}\sqrt{\frac{E}{\rho}}, \tag{1}$$

where L is the length of the resonator and parameters E and ρ are the effective Young's modulus and mass density of the sensor respectively.

When thickness and width are comparable yet considerably smaller than the length, the strip is considered as being in a state of plane strain. In such case the plane-strain Young's modulus can be expressed as:

$$E_{plane-strain} = \frac{E}{1-v^2}, \tag{2}$$

where v is the Poisson's ratio of the material.

For a slender freestanding strip, the natural frequency relation should be modified using the plane-stress or biaxial modulus as:

$$E_{plane-stress} = \frac{E}{1-v} \tag{3}$$

The first order frequency is then:

$$f_0 = \frac{1}{2L}\sqrt{\frac{E}{(1-4)\rho}} \tag{4}$$

Assuming there is a solid, continuous mass uniformly deposed onto the magneto-elastic strip's surface, the change of the resonant frequency is approximated as:

$$\Delta f = \frac{1}{2}\left(\frac{\Delta E}{E} - \frac{\Delta m}{m}\right)f_0, \tag{5}$$

where Δf, ΔE and Δm are the changes of resonant frequency, effective Young's modulus, and mass of the resonator due to the material deposition, respectively.

In physics and mechanics, mass distribution is the spatial distribution of mass within a solid body. The mass is considered as distributed mass in the magneto-mechanical system when the mass is disposed continuously on the resonator surface, for example, as a uniform thin film coating. For first order stationary longitudinal vibration of the magneto-elastic strip with uniformly distributed mass, the vibration of the strip can be assumed as:

$$u(x,t) = A(t)\sin\left(\frac{\pi}{2l}x\right) \tag{6}$$

where u(x,t) is the displacement at the location x and t is the time variable, respectively. The original point is assumed at the center of the long axis of the strip, l is half of the strip length L, A(t) is the vibration amplitude variable that assumed at specific time t. The center is the stationary node and the two ends have the largest vibration amplitude. The kinetic energy $T_d$ due to the uniformly distributed mass is then:

$$T_d = 2*\frac{1}{2}\int_0^l \rho S\left(\frac{du(x,t)}{dt}\right)^2 dx = \int_0^l \rho S\left(A(t)\sin\left(\frac{\pi}{2l}x\right)\right)^2 dx \tag{7}$$

$$T_d = \rho S A(t)^2 \frac{2l}{\pi}\left(\frac{\frac{\pi}{2l}x}{2} - \frac{1}{2}\sin\left(\frac{\pi}{2l}x\right)\cos\left(\frac{\pi}{2l}x\right)\right)\Big|_{x=0}^{x=l} \tag{8}$$

$$T_d = \frac{1}{2}A(t)^2 \rho S l \tag{9}$$

$$T_d = \frac{1}{2}A(t)^2 * \left[\frac{1}{2}M_0\right] \tag{10}$$

where $M_o$ is the initial strip mass:

$$M_0 = \rho s L = 2\rho s l \tag{11}$$

Figure 2A:
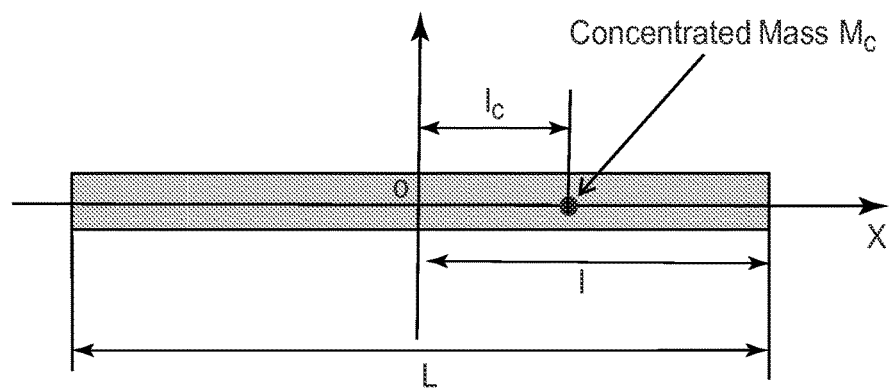
FIG. 2A is a schematic physical model of a sensor.

In theory, concentrated mass is considered as point mass. FIG. 2A is a schematic physical model of a resonator. The dimensions in the transverse dimensions of width and thickness are relatively smaller than the longitudinal dimension, for example, the width being ⅕ of length. The longitudinal length is L. The length l is half of the longitudinal length L.

The center of the resonator is a vibration node and is assumed as the original point O in the longitudinal axial. To illustrate the effects of concentrated mass on sensor response, a concentrated mass $M_c$ is assumed to be positioned on the sensor surface at the location of distance $l_c$ from the original point O.

Figure 2B:
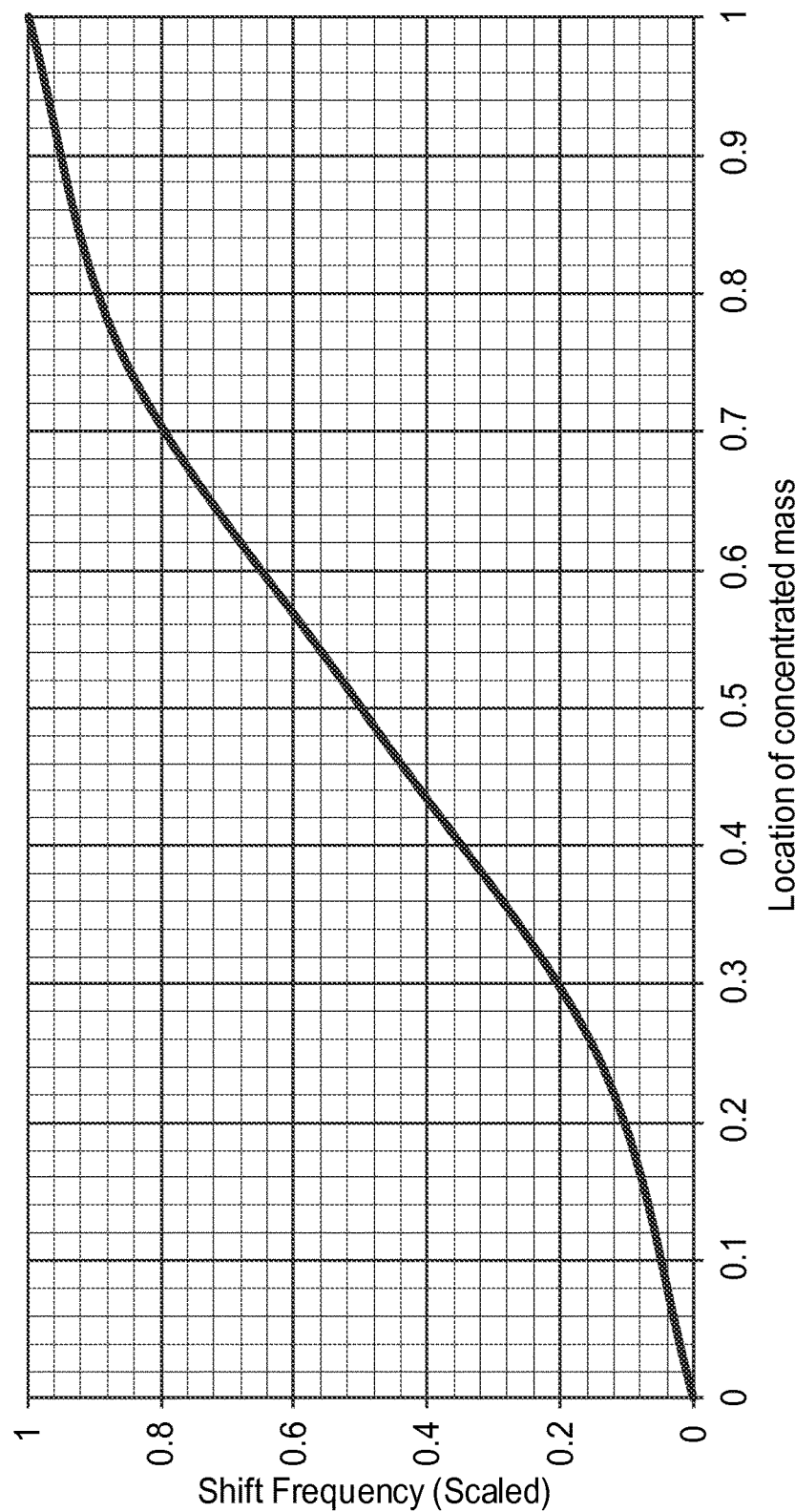
FIG. 2B illustrates frequency shifts due to mass location.

In actual implementations, concentrated mass is a collection or aggregation of mass where its dimensions are significantly smaller than the resonator surface. For example, concentrated mass is a small amount of biological cells attached to the resonator in a biological detection system. When concentrated mass is attached to the resonator, the following equation is obtained:

$$\Delta f = f_0 \left( -\frac{2M_c}{M_0} \left( \sin\left(\frac{\pi}{2l} l_c\right) \right)^2 \right), \quad (12)$$

where $M_c$ is the concentrated mass of the environmentally responsive material and $l_c$ is the location of the concentrated mass on the resonator 130. The frequency shift due to the concentrated mass disposed at different locations along the longitudinal axis is shown in FIG. 2B. The frequency shift is scaled with the frequency shift of the concentrated mass $M_c$ located at the end side of the sensor. As illustrated, the frequency shift is related to the location of the concentrated mass. The location of the concentrated mass (distance from the center) is scaled with the length of the resonator, while distance 0 and 1 represent the concentrated mass located at the center and the far end, respectively.

As illustrated in FIG. 2B, a greater shift in frequency is evident when the concentrated mass is moved away from the center of the resonator. While there is no motion (or zero kinetic energy) at the stagnant node, kinetic energy becomes increasingly available in positions moving from the center towards the end of a resonator. Therefore, a given concentrated mass attached to the resonator end can have more impact to the frequency response of the resonator.

For distributed mass deposition, such as materials flowing from the center, assumed constant material density during flow, the effective deposited mass is:

$$M_{t-effective} = \rho_2 S_2 \left( l_t - \frac{1}{\pi} \sin\left(\frac{\pi}{2l} l_t\right) \cos\left(\frac{\pi}{2l} l_t\right) \right) \quad (13)$$

where $l_t$, $\square_2$ and $S_2$ are flow distance, mass density and cross section area of the flow mass, respectively. The effective deposited mass is calculated based on the assumption that the mass flow uniformly along the longitude direction. A frequency shift is not evident if the concentrated mass is disposed at the center of the sensor. However, relative large frequency shifts happen when the mass flows to the end of the sensor.

$$M_{t-effective} = 0, \text{ when } l_t = 0; \quad (14a)$$

$$M_{t-effective} = \rho_2 S_2 l, \text{ when } l_t = 1 \quad (14b)$$

For distributed mass deposition, the frequency shift is:

$$\Delta f = f_0 \left( -\frac{1}{2} \right) \frac{\rho_2}{\rho} \frac{S_2}{S} \left( \frac{l_t}{L} - \frac{1}{2\pi} \sin\left(\frac{\pi}{2l} l_t\right) \cos\left(\frac{\pi}{2l} l_t\right) \right) \quad (15)$$

Figure 2C:
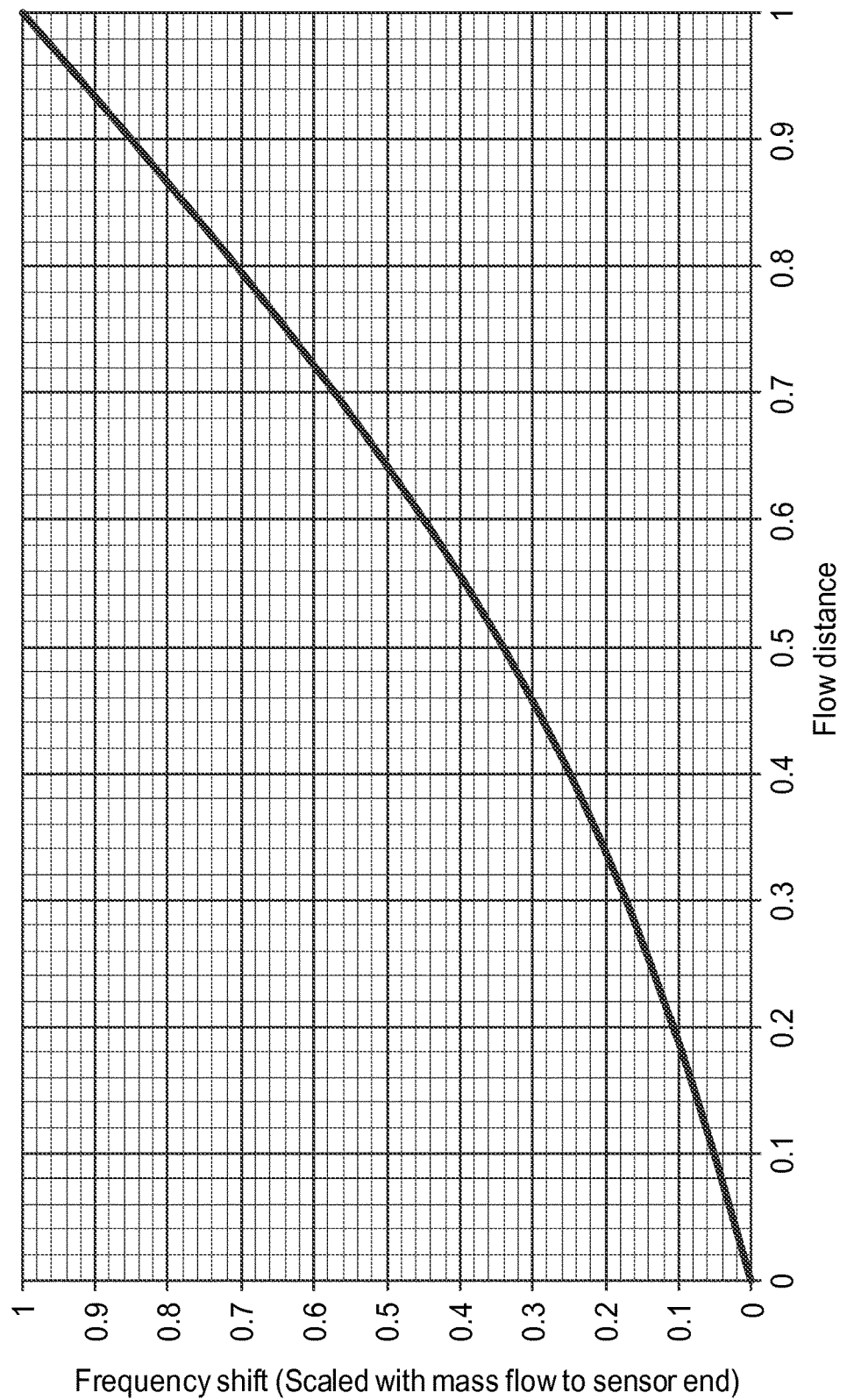
FIG. 2C illustrates frequency shifts due to mass distribution.

For distributed mass deposition, the frequency shift due to mass flow is shown in FIG. 2C. The flow distance is scaled with the sensor length, while flow distance 0 represents mass at the sensor center. When the mass flows to the sensor end, the flow distance is 1. The frequency shift is scaled with the frequency shift of the flow mass reached the end side of the sensor. The frequency shift is directly related to initial frequency, flowed mass density, coating thickness and flow distance.

According to these principles, it is not only the adding or subtracting of mass that changes the resonator resonant frequency but also changing the mass distribution changes the frequency. Redistributing mass from the center to end(s) of the resonator decreases the resonant frequency; conversely, shifting mass from the end(s) of the resonator to the center increase(s) the resonant frequency.

Figure 3A:
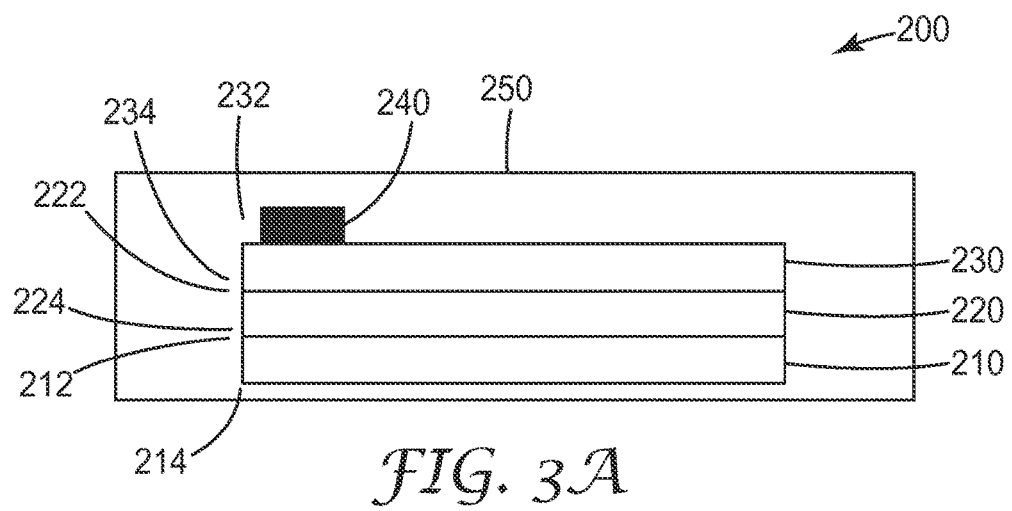
FIG. 3A is a side view of one embodiment of an MMR sensor.
Figure 3B:
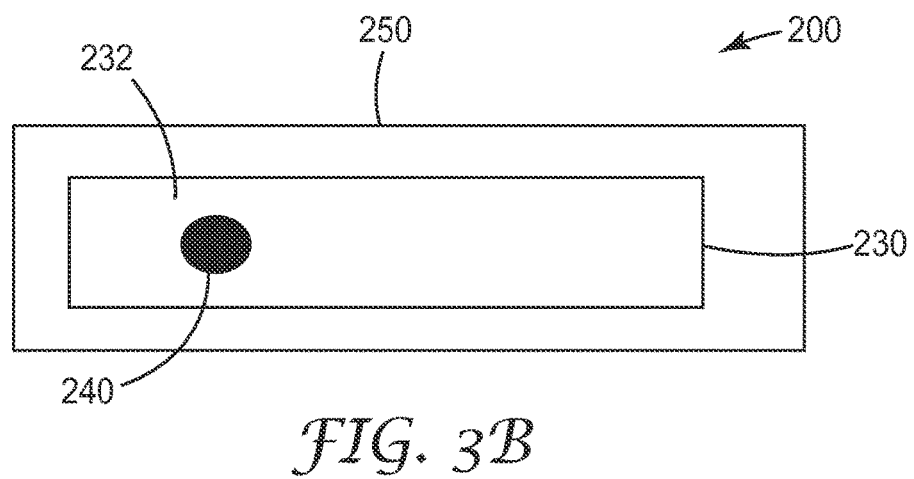
FIG. 3B is a top plane view of the MMR sensor illustrated in FIG. 3A with cover lifted.
Figure 3C:
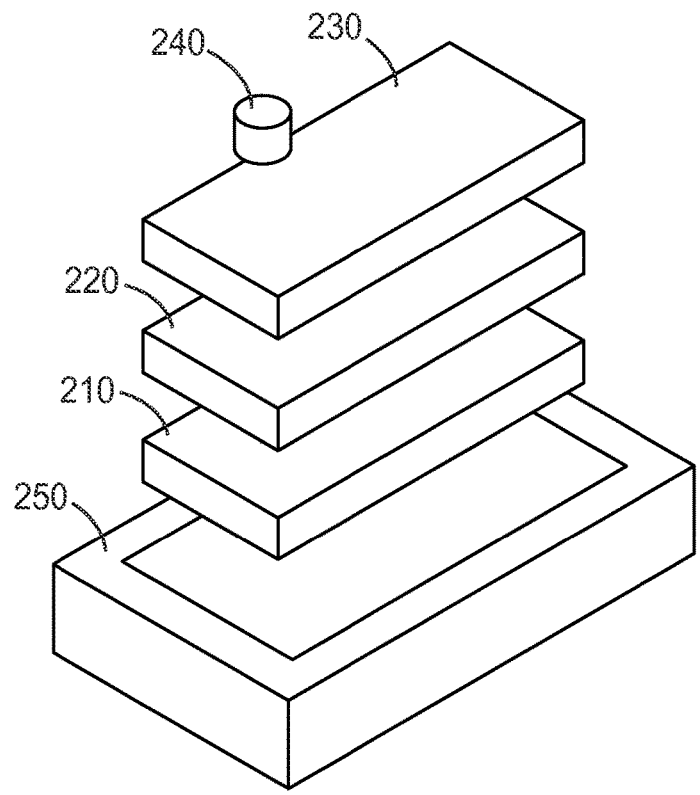
FIG. 3C is an exploded view of the MMR sensor illustrated in FIG. 3A.

FIG. 3A is a side view of one embodiment of an MMR sensor 200. FIG. 3B is a top plane view of the MMR sensor 200 with cover lifted and FIG. 3C is an exploded view of the MMR sensor 200. In the embodiment illustrated, the sensor 200 includes a magnetic bias layer 210, a spacer 220, a resonator 230, an environmental change receptor 240, and an optional housing 250. The magnetic bias layer 210, the spacer 220, the resonator 230, and the environmental change receptor 240 are contained in the housing 250. The magnetic bias layer 210, the spacer 220, the resonator 230, and the environmental change receptor 240 can have the same or similar compositions as the corresponding components illustrated in FIGS. 1A-1C.

The magnetic bias layer 210 has a first magnetic surface 212 and an opposing second magnetic surface 214. The spacer 220 is disposed between the magnetic bias layer 210 and the resonator 230. The spacer 220 having a first spacer surface 222 and an opposing second spacer surface 224. The second spacer surface 224 is adjacent to the first magnetic surface 212. The resonator 230 has a first resonator major surface 232 and an opposing second resonator major surface 234. The second resonator major surface 234 is facing toward to the first magnetic surface 212. As illustrated, the environmental change receptor 240 is disposed proximate to one edge of the first major resonator surface. Typically, the environmental change receptor 240 may vary its volume or disposition in response to environmental changes, such as water flow or gas flow. In some cases, the first resonator surface 232 can have a predefined channel (not shown in the figure) that allowing the environmental change receptor 240 to flow along at least part of the predefined channel in response to environmental changes.

Figure 3D:
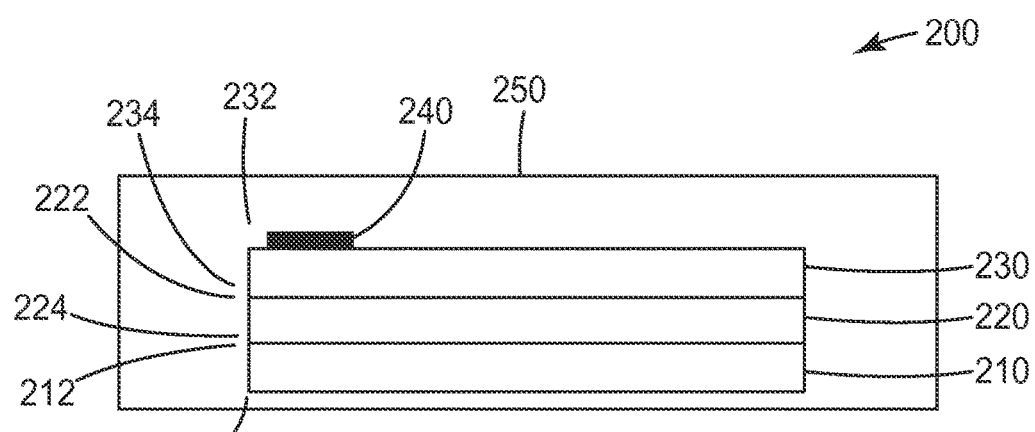
FIG. 3D is a side view illustrating an example of the MMR sensor illustrated in FIG. 3A after environment changes.

FIG. 3D is a side view illustrating an example of the MMR sensor 200 after environment changes. The environmental change receptor 240 reduces its volume in response to changes to the environmental variables, such as going through a wash cycle. The mass of the resonator 230 is changed because of the volume reduction of the environmental change receptor 240 on the resonator 230.

Figure 4A:
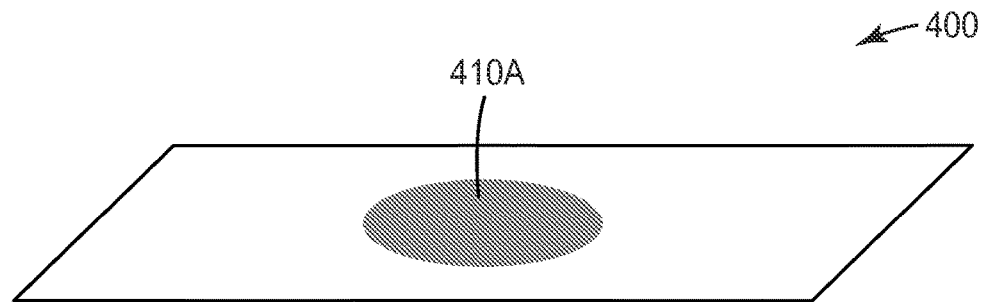
FIGS. 4A-4F illustrate some examples of predefined channel configurations.
Figure 4B:
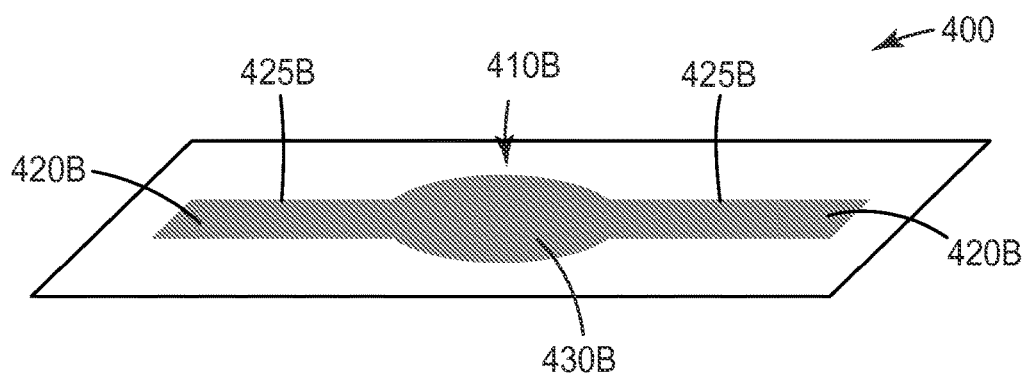
Figure 4C:
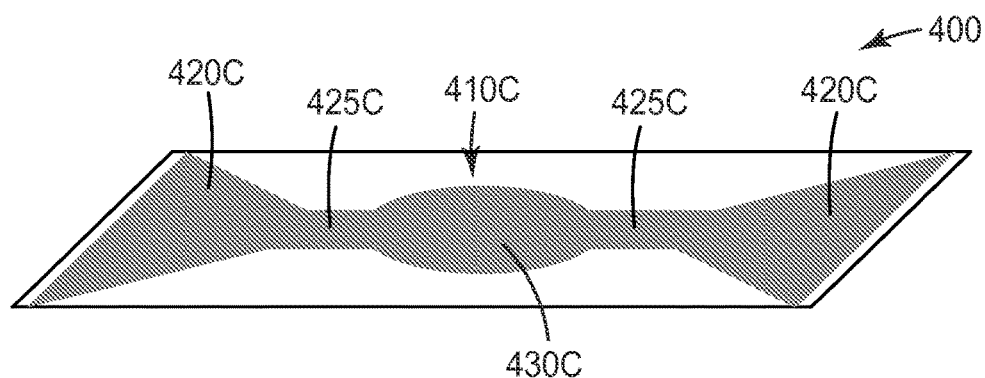

FIGS. 4A-4F illustrate some examples of predefined channels on resonators 400. FIG. 4A illustrates a predefined channel 410A in an oval shape. FIG. 4B illustrates a predefined channel 410B having a center portion 430B in an oval shape and two end portions 420B, and paths 425B between the center portion 430B and the end portions 420B. The width of the end portion 420B is similar to the width of the path 425B. FIG. 4C illustrates a predefined channel 410C having a center portion 430C in an oval shape, two end portions 420C, and paths 425C between the center portion 430C and the end portions 420C. The end portion 420C is in a triangular shape that becomes wider toward the end.

Figure 4D:
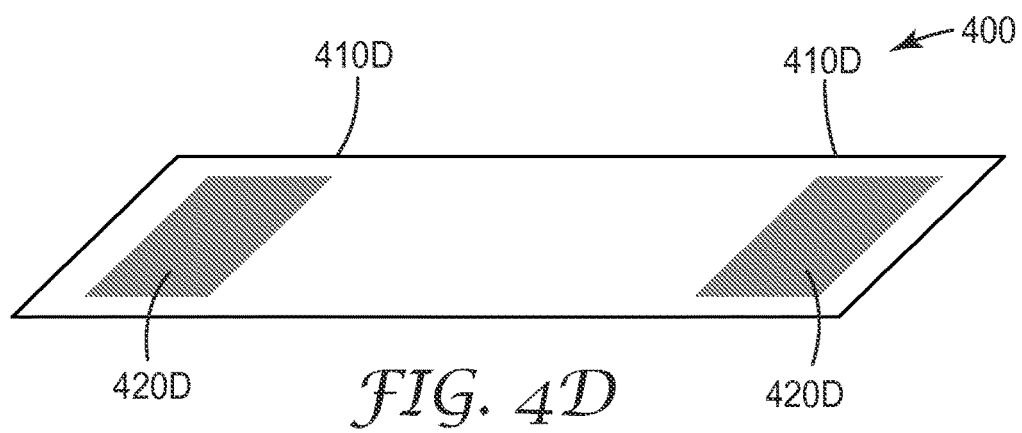

FIG. 4D illustrates a predefined channel 410D having two end portions 420D, each end portion in a rectangular shape.

Figure 4E:
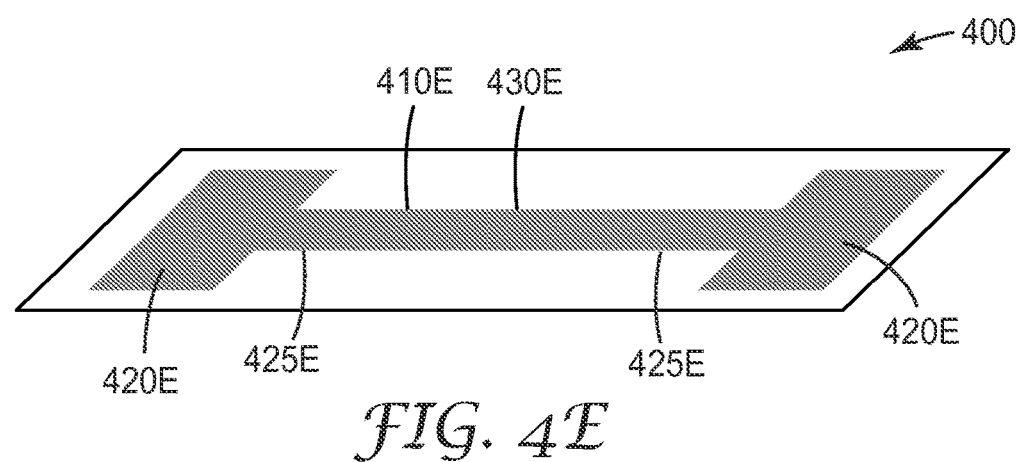
Figure 4F:
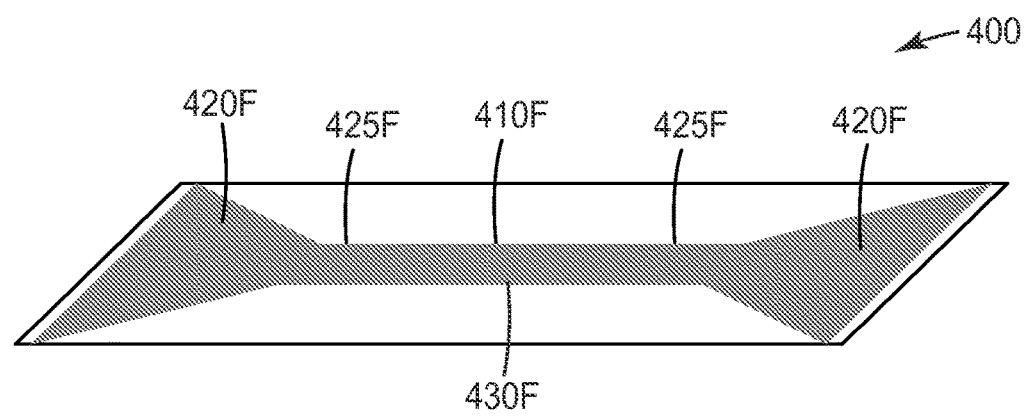

FIG. 4E illustrates a predefined channel 410E having a center portion 430E, two end portions 420E, and paths 425E between the center portion 430E and the end portions 420E. The width of the end portion 420E is wider than the width of the path 425E. FIG. 4F illustrates a predefined channel 410F having a center portion 430F, two end portions 420F, and paths 425F between the center portion 430F and the end portions 420F. The end portion 420F is in a triangular shape that becomes wider toward the end.

Figure 5A:
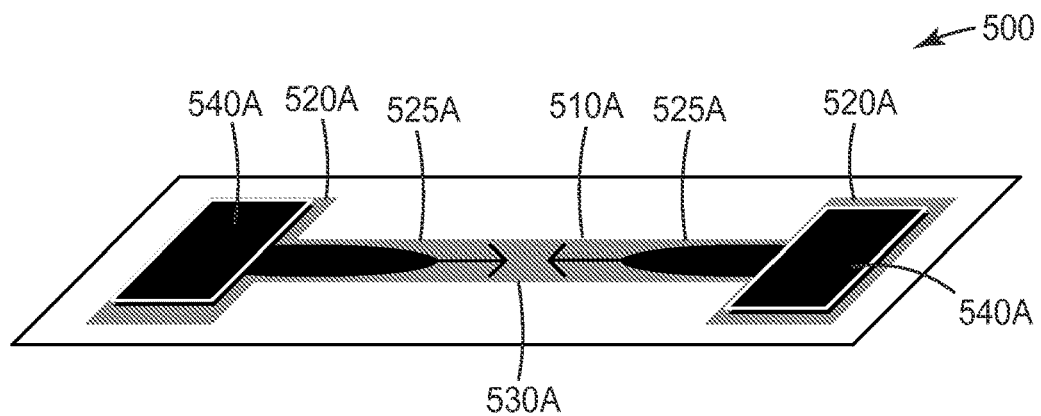
FIGS. 5A-5G illustrate some examples of channel configurations and mass distribution on a resonator during and after environmental changes.

FIG. 5A-5G illustrate some examples of channel configurations and mass distribution on a resonator 500 during and after environmental changes. FIG. 5A illustrates a channel 510A that has a center portion 530A, two end portions 520A, and paths 525A connecting the center portion 530A and the end portions 520A. The end portion 520A is in a generally rectangular shape. Environmental change receptor 540A is disposed at both end portions 520A and distributes along the paths 525A toward the center portion 530A in response to environmental change(s).

Figure 5B:
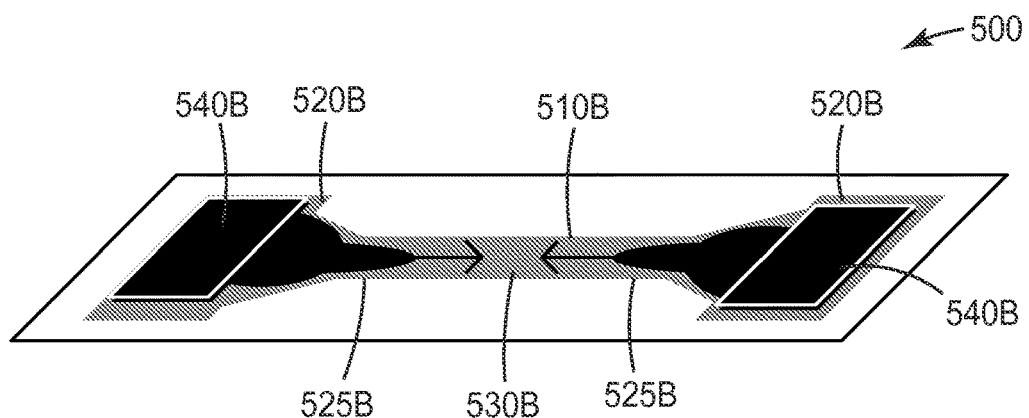
Figure 5C:
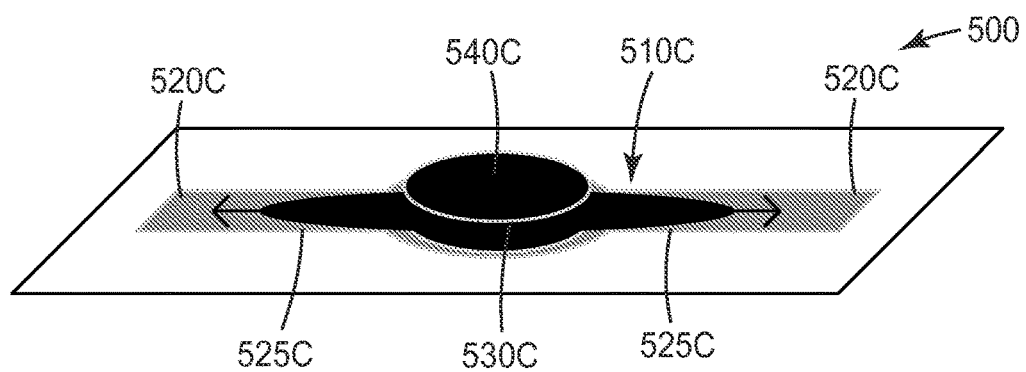

FIG. 5B illustrates a channel 510B that has a center portion 530B, two end portions 520B, and paths 525B connecting the center portion 530B and the end portions 520B. The end portion 520B is in a generally rectangular shape. The paths 525B are gradually wider close to the end portions 520B. Environmental change receptor 540B is disposed at both end portions 520B and distributes along the paths 525B toward the center portion 530B in response to environmental change(s). FIG. 5C illustrates a channel 510C has a center portion 530C, two end portions 520C, and paths 525C connecting the center portion 530C and the end portions 520C. The center portion 530C is in a generally oval shape. The end portion 520C and the path 525C have a same width. Environmental change receptor 540C is disposed at the center portion 530C and distributes along the paths 525C toward the end portions 520C in response to environmental change(s).

Figure 5D:
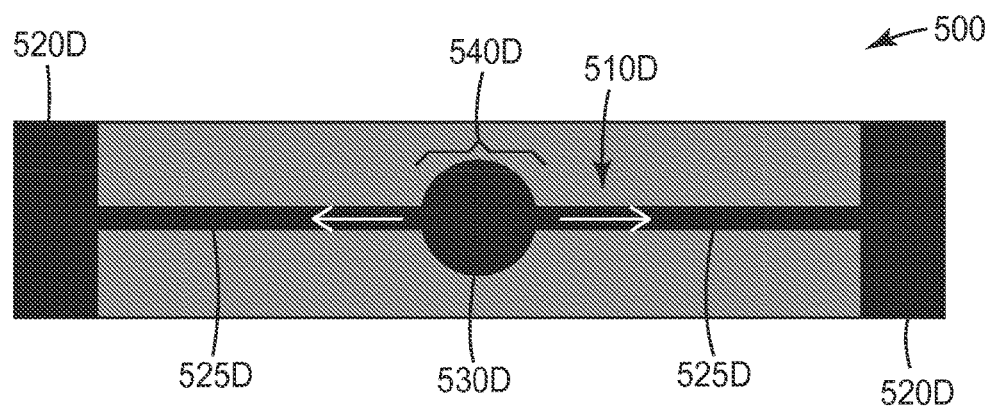

FIG. 5D illustrates a channel 510D having a center portion 530D, two end portions 520D, and paths 525D connecting the center portion 530D and the end portions 520D. The center portion 530D is in a generally round shape. The end portions 520D are in a generally rectangular shape. Environmental change receptor 540D is disposed at the center portion 530D and distributes along the paths 525D toward the end portions 520D in response to environmental change(s).

Figure 5E:
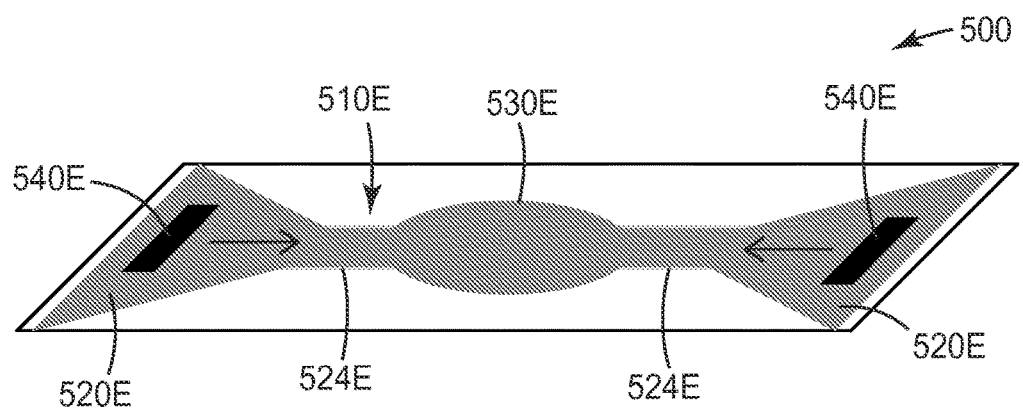

FIG. 5E illustrates a channel 510E that has a center portion 530E, two end portions 520E, and paths 524E connecting the center portion 530E and the end portions 520E. The center portion 530E is in a generally oval shape. The end portions 520E are in a triangular shape becoming wider close to the edge. Environmental change receptor 540E is disposed at the end portions 520E and distributes along the paths 524E toward the center portion 530E in response to environmental change(s).

Figure 5F:
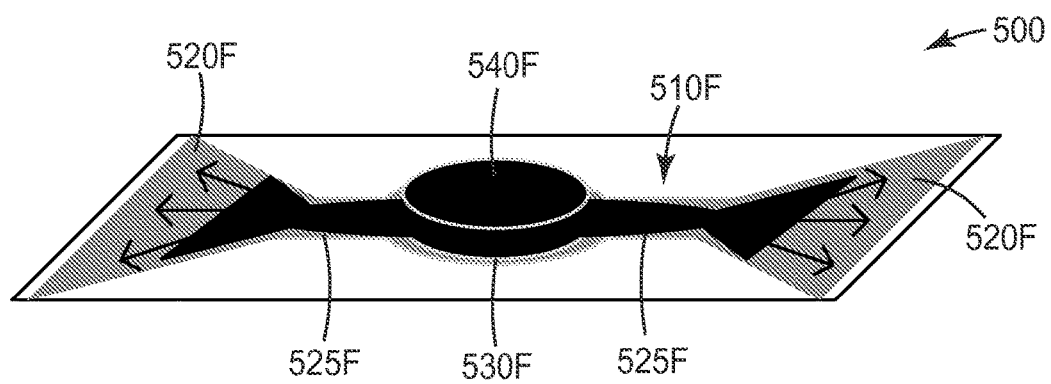

FIG. 5F illustrates a channel 510F that has a center portion 530F, two end portions 520F, and paths 525F connecting the center portion 530F and the end portions 520F. The center portion 530F is in generally oval shape. The end portions 520F are in triangular shape becoming wider close to the edge. Environmental change receptor 540F is disposed at the center portions 530F and distributes along the paths 525F toward the end portions 520F in response to environmental change(s).

Figure 5G:
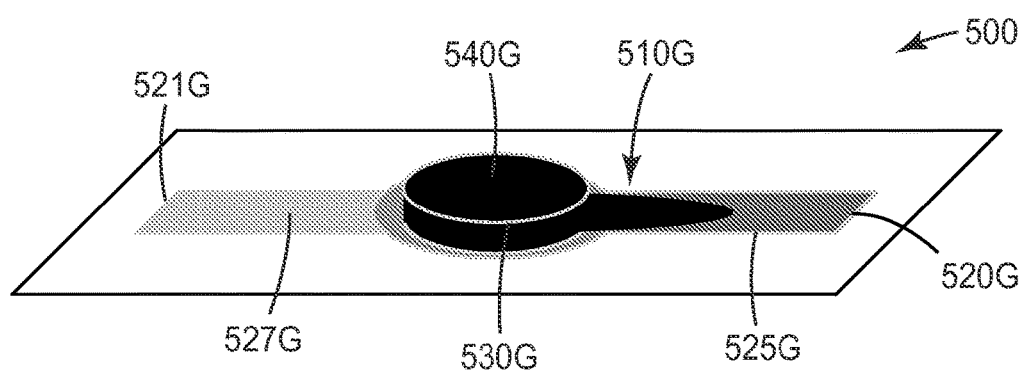

FIG. 5G illustrates a channel 510G that has a center portion 530G, one end portion 520G, one end portion 521G, a flow-philic path 525G connecting the center portion 530G and the end portion 520G, and a flow-phobic path 527G connecting the center portion 530G and the end portion 521G. The center portion 530G is in a generally oval shape. Environmental change receptor 540G is disposed at the center portion 530G and distributes along the path 525G toward the end portion 520G but not along the path 527G.

Figure 6A:
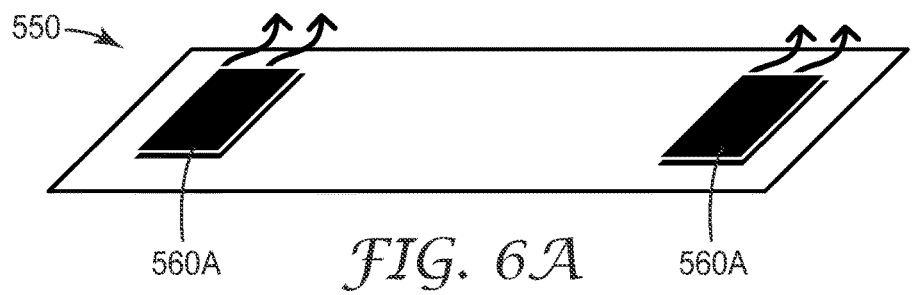
FIGS. 6A-6D illustrate some examples of pre-disposing environmental change receptors on a resonator.
Figure 6B:
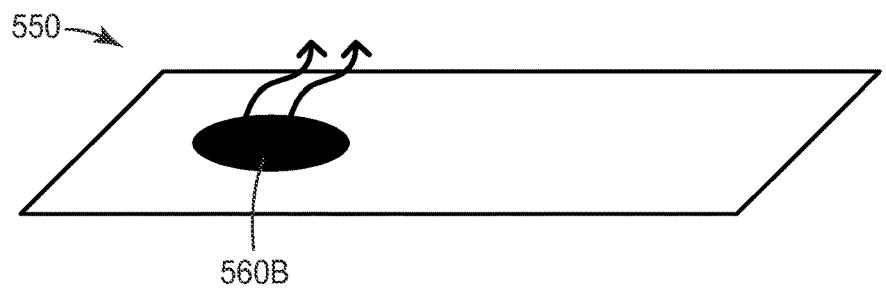
Figure 6C:
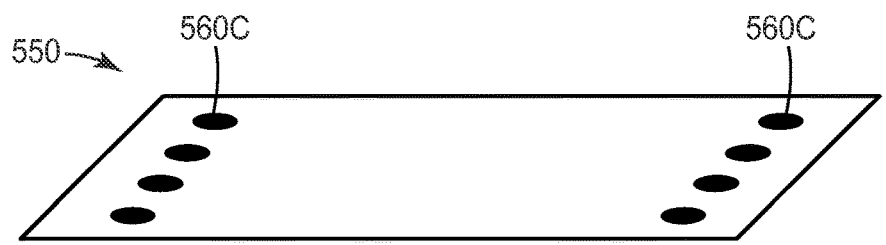
Figure 6D:
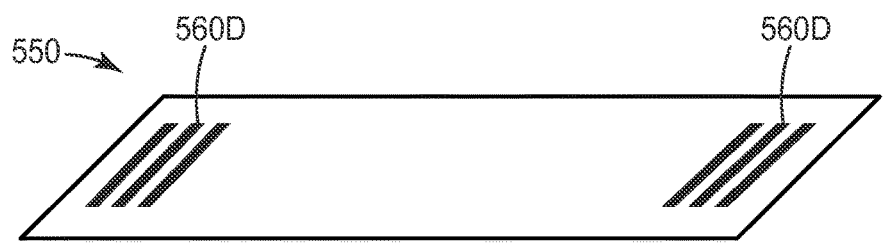

FIGS. 6A-6D illustrate some examples of pre-disposing environmental change receptors on a resonator 550, whose properties are typically changed when interacting with fluid. In some embodiments, the weight of the environmental change receptor is reduced in response to environmental changes. For example, at least part of the environmental change receptor is washed off when the sensor is disposed in a washer. In some other embodiments, the environmental change receptor absorbs fluid and the weight is increased in response to environmental changes. For example, the environmental change receptor absorbs gas and/or liquids and becomes heavier. FIG. 6A shows environmental change receptor 560A including two receptor elements, each element being disposed proximate to an edge of the resonator 550. FIG. 6B shows environmental change receptor 560B including one receptor element disposed to a side of the resonator 550. FIG. 6C shows environmental change receptor 560C including two receptor parts, each part being disposed to proximate to an edge of the resonator 550. Each part of the receptor 560C includes a dot pattern of distribution of receptor elements. FIG. 6D shows environmental change receptor 560D including two parts, each part being disposed to proximate to an edge of the resonator 550. Each part of the receptor 560D includes a line pattern of distribution of receptor elements.

Figure 7A:
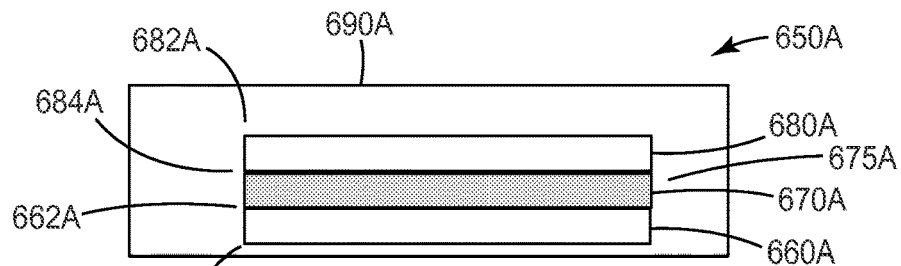
FIG. 7A illustrates a cross-sectional view of one embodiment of a MMR sensor.
Figure 7B:
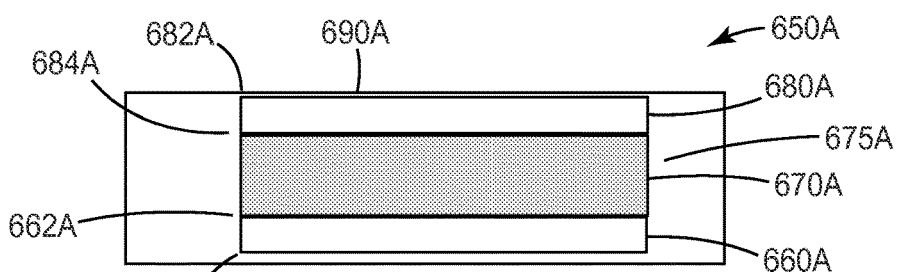
FIG. 7B illustrates a cross sectional view of an example of the MMR sensor illustrated in FIG. 7A after it interacts with fluid.

FIG. 7A illustrates a cross-sectional view of one embodiment of a MMR sensor 650A. In the embodiment illustrated, the sensor 650A includes a magnetic bias layer 660A, a spacer 670A, a resonator 680A, and an optional housing 690A. The magnetic bias layer 660A, the spacer 670A, and the resonator 680A are disposed in the housing 690A. The magnetic bias layer 660A, the spacer 670A, and the resonator 680A can have the same or similar compositions as the corresponding components illustrated in FIGS. 1A-1C. The magnetic bias layer 660A has a first magnetic surface 662A and an opposing second magnetic surface 664A. The spacer 670A is disposed between the magnetic bias layer 660A and the resonator 680A. The resonator 680A has a first resonator major surface 682A and an opposing second resonator major surface 684A. The second resonator major surface 684A is facing toward the first magnetic surface 662A. In the embodiment illustrated, the spacer 670A includes an environmental change receptor 675A that is configured to rapidly expand when it absorbs fluid. In some embodiments, the environmental change receptor 675A can include a porous material, such as a natural or synthetic sponge, water-absorbing gel, superabsorbent polymer, or the like. Sponges may be made from cellulose, polyester or other polymers. Superabsorbent polymers may include polyacrylate/polyacrylamide copolymers, polyvinyl alcohol copolymers, for example. FIG. 7B illustrates a cross sectional view of an example of the MMR sensor 650A after it interacts with fluid. After the thickness of the spacer 670A is increased, the resonator 680A is damped and its resonance frequency is shifted or extinguished.

Figure 7C:
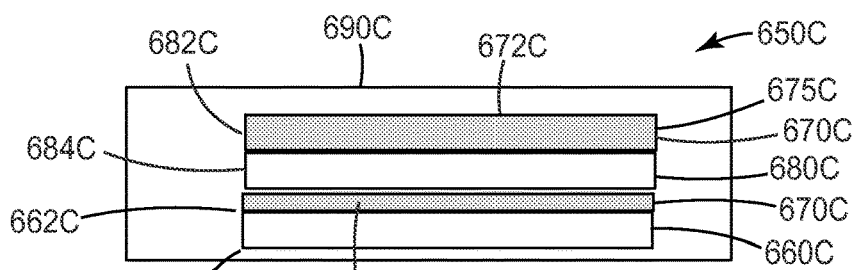
FIG. 7C illustrates a cross-sectional view of another embodiment of a MMR sensor.
Figure 7D:
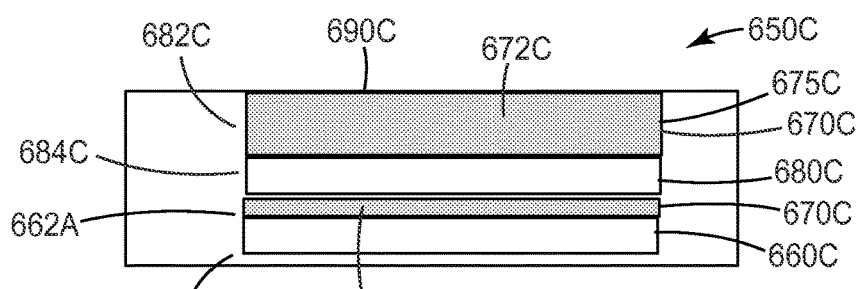
FIG. 7D illustrates a cross sectional view of an example of the MMR sensor illustrated in FIG. 7C after it interacts with fluid.

FIG. 7C illustrates a cross-sectional view of another embodiment of a MMR sensor 650C. In the embodiment illustrated, the sensor 650C includes a magnetic bias layer 660C, a spacer 670C, a resonator 680C, and an optional housing 690C. The magnetic bias layer 660C, the spacer 670C, and the resonator 680C are contained in the housing 690C. In this configuration, the spacer 670C includes two parts: one part 671C of the spacer 670C is disposed between the magnetic bias layer 660C and the resonator 680C and another part 672C is disposed between the resonator 680C and the housing 690C. The magnetic bias layer 660C, the spacer 670C, and the resonator 680C can have the same or similar compositions as the corresponding components illustrated in FIGS. 1A-1C. The magnetic bias layer 660C has a first magnetic surface 662C and an opposing second magnetic surface 664C. The resonator 680C has a first resonator major surface 682C and an opposing second resonator major surface 684C. The second resonator major surface 684C is facing toward the first magnetic surface 662C. In the embodiment illustrated, the spacer part 672C includes an environmental change receptor 675C that is configured to rapidly expand when it absorbs fluid. In some embodiments, the environmental change receptor 675C can include a porous material, such as a natural or synthetic sponge, water-absorbing gel, superabsorbent polymer, or the like. Sponges may be made from cellulose, polyester or other polymers. Superabsorbent polymers may include polyacrylate/polyacrylamide copolymers, polyvinyl alcohol copolymers, for example. FIG. 7D illustrates a cross sectional view of an example of the MMR sensor 650C after it interacts with fluid. After the thickness of the spacer 670C is increased, the resonator 680C is damped and its resonance frequency is shifted or extinguished.

Figure 8G:
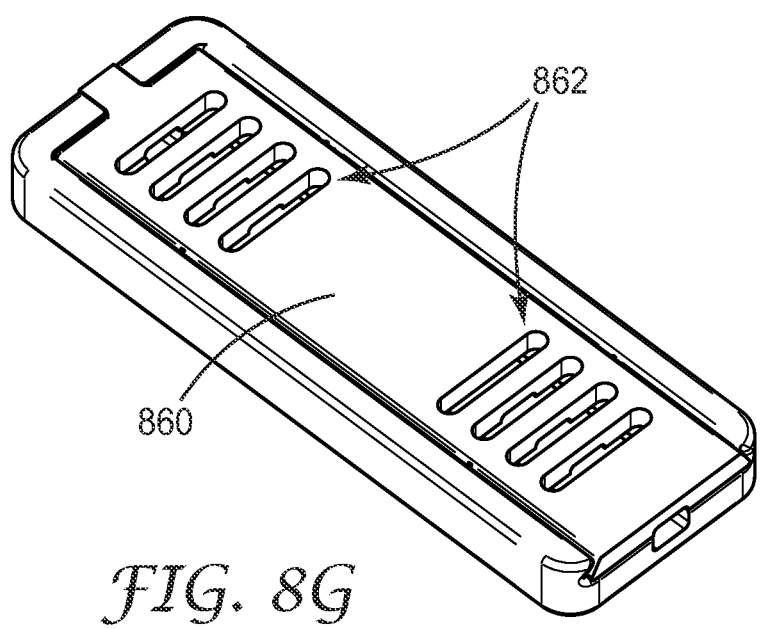

FIGS. 8A-8H illustrate some examples of MMR sensors 800 with different housing constructions. FIG. 8A is a cross sectional view of one embodiment of a MMR sensor 800, and FIG. 8B is a top view of the MMR sensor 800 illustrated in FIG. 8A with cover lifted. The MMR sensor 800 includes a housing 850, a magnetic bias layer 810, a spacer 820, a resonator 830. The housing 850 includes a case 855 and a cover 860. The cover may have openings 862 to allow the resonator to interact with environmental elements, as an example of housing illustrated in FIG. 8G. The openings 862 can have any shapes, for example, rectangular, oval, circle, wavy, irregular shapes, or the like. In some implementations, the housing or part of the housing can use materials with selective permeability.

FIG. 8C is a cross sectional view of one embodiment of a MMR sensor 800, and FIG. 8D is a top view of the MMR sensor 800 illustrated in FIG. 8C with cover lifted. In the embodiment illustrated, the housing 850 includes pointed structures 843 to support the resonator 830 and point structure 840 to create space between the housing 850 and the resonator 830 in order to reduce interaction between the housing 850 and the resonator 830. The cover 860 may also have pointed structures to support or confine the resonator 830 to reduce interaction between the housing 850 and the resonator 830. The housing 850 may include two separate chambers 852 and 854. The magnetic bias layer 810 is disposed in the chamber 852 and the resonator 830 is disposed in the chamber 854. In some cases, the chamber 854 has openings to allow the interaction of the resonator 830 with environmental elements.

FIG. 8E is a cross sectional view of one embodiment of a MMR sensor 800, and FIG. 8F is a top plane view of the MMR sensor 800 illustrated in FIG. 8E with cover lifted. In the embodiment illustrated, the housing 850 includes supporting structure 844 to support the resonator 830. The housing 850 may include two separate chambers 852 and 854. The magnetic bias layer 810 is disposed in the chamber 852 and the resonator 830 is disposed in the chamber 854. In some cases, the chamber 854 has openings to allow the interaction of the resonator 830 with environmental elements.

Figure 8H:
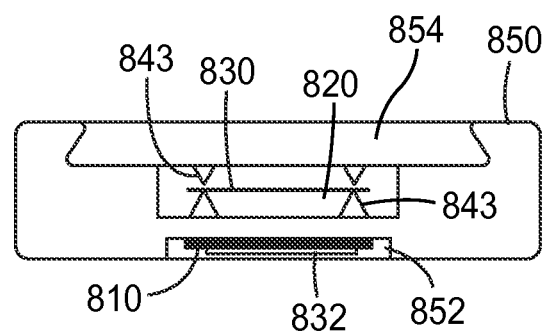

In some embodiments, as illustrated in FIG. 8H, the MMR sensor 800 may have more than one resonator 830 and 832 and one magnetic bias layer 810. The housing 850 may include two separate chambers 852 and 854. The magnetic bias layer 810 and the resonator 832 with a spacer (not illustrated) are disposed in the chamber 852 and the resonator 830 is disposed in the chamber 854. In some cases, the chamber 854 has openings to allow the interaction of the resonator 830 with environmental elements. In some cases, the resonator 832 can function as a control whose resonant frequency will not change during course of measurement of environmental changes.

Figure 9A:
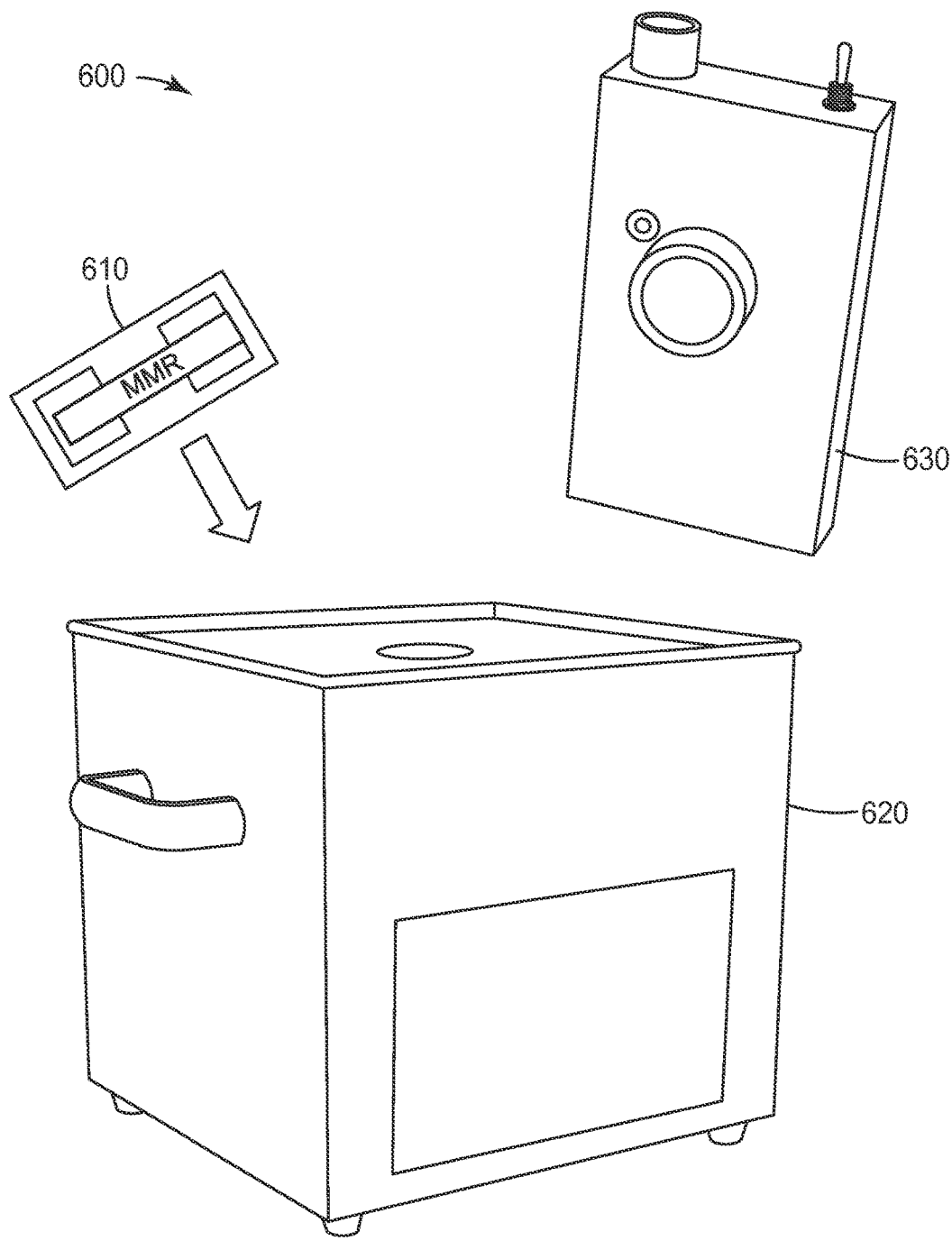
FIG. 9A illustrates one embodiment of a sensing system using one or more MMR sensors.

FIG. 9A illustrates one embodiment of a sensing system 600 using one or more MMR sensors. In the embodiment as illustrated, the sensing system 600 includes an MMR sensor 610 to be disposed in an environment 620. The environment 620 can be an enclosed environment (e.g., washer, sterilizer, etc.) or an open environment (e.g., soil, water, air, etc.). The MMR sensor 610 can be any one of the MMR sensors described in the present disclosure. The sensing system 600 includes a reader 630. The reader 630 is configured to measure frequency characteristic of the MMR sensor 610. In some cases, the reader 630 takes one measurement of the frequency characteristic of the MMR sensor 610 after an environmental variable has changed. The reader 630 or some other computing devices can determine whether the environmental variable has changed above a predetermined threshold or below the predetermined threshold based on the frequency measurement. In some other cases, the reader 630 can measure a before-change frequency characteristic of the MMR sensor before the environmental variable has changed and an after-change frequency characteristic of the MMR sensor after the environmental variable has changed. In such cases, the reader 630 or some other computing devices can determine whether the environmental variable has changed above a predetermined threshold or below the predetermined threshold based on the frequency measurement based on the before-change frequency characteristic and the after-change frequency characteristic.

In some embodiments, the reader 630 includes electromagnetic excitation circuit controls, generates and launches electromagnetic waves to excite the MMR sensor 610. This excitation provides power to the MMR sensor 610 that is converted and stored as oscillatory motion, where the stored energy is cyclically changing between kinetic and potential energy. When the excitation is removed, the MMR sensor 610 dissipates the stored energy in the form of motion, radiated acoustic and electromagnetic energy, to be detected by the reader 630. In some embodiments, the reader 630 can measure a sequence of frequency characteristic of the MMR sensors to monitor the change to the environmental variable. In some cases, the reader 630 is configured to determine the frequency where the resonator response is at maximum.

In some embodiments, the reader 630 is an oscillator that may sweep through a range of frequencies, and a microphone to acoustically detect the response of the sensor while it is being energized. The sensor response will be a maximum when the energizing frequency matches the resonant frequency, allowing measurement of any resonant frequency shift due to changes in environmental variables.

Any of the previous equations relating change in frequency to changes in MMR sensor parameters may be rearranged to calculate sensor parameter changes as a function of frequency change. For example, equation (5) can be rearranged as:

$$\left(\frac{\Delta E}{E} - \frac{\Delta m}{m}\right) = 2\frac{\Delta f}{f_0} \quad (16)$$

In some embodiments, the reader is designed to sweep through a range of frequencies to determine the resonant frequency of the MMR sensor before and after some environmental change has occurred, and thus measure the relative frequency shift due to changes in sensor parameters. The sensor parameters (e.g. change in mass distribution) in turn are related to environmental changes through some physical process, for example, such as melting and flowing (along a controlled channel) of a wax pellet on the sensors.

Figure 10:
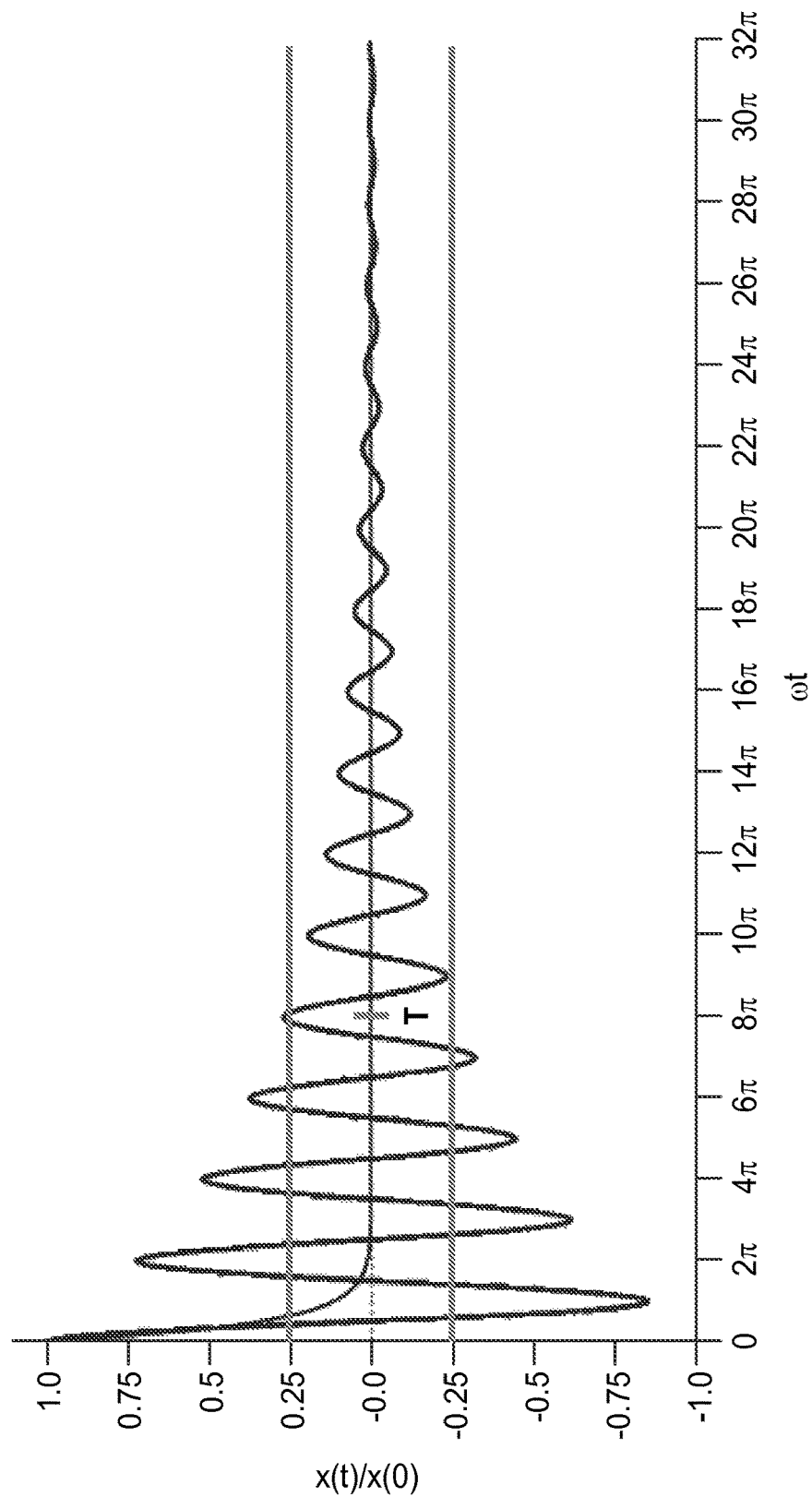
FIG. 10 illustrates a graph of an example of MMR sensor's resonance signal.

The reader 630 can use a number of detection methods. For example, the reader 630 can include an impedance analyzer. The impedance of the MMR sensor 610 increases when its magnetic permeability increases when the sweeping frequency moves toward its resonant frequency and at its maximum when the sweeping frequency is at the resonant frequency. As another example, the reader 630 can include a spectrum analyzer (e.g., an ultrasonic microphone, etc.) while the resonance movement of the MMR sensor can be detected as sound wave, for example, in the range of 30 kHz-100 kHz. As yet another example, the reader 630 can include a motion detection device to observe the sensor displacement. In some cases, the reader 630 can measure the duration of time (T) for the MMR sensor's resonance signal to decay (ring-down) to a predetermined level, as illustrated in FIG. 10.

Figure 9B:
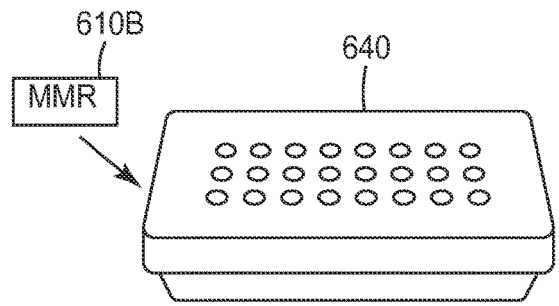
FIGS. 9B-9D illustrate another embodiment of a sensing system using one or more MMR sensors disposed in a container.
Figure 9C:
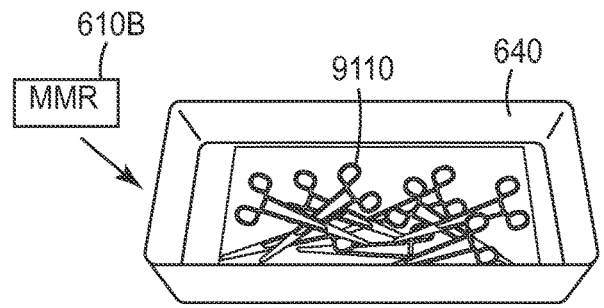
Figure 9D:
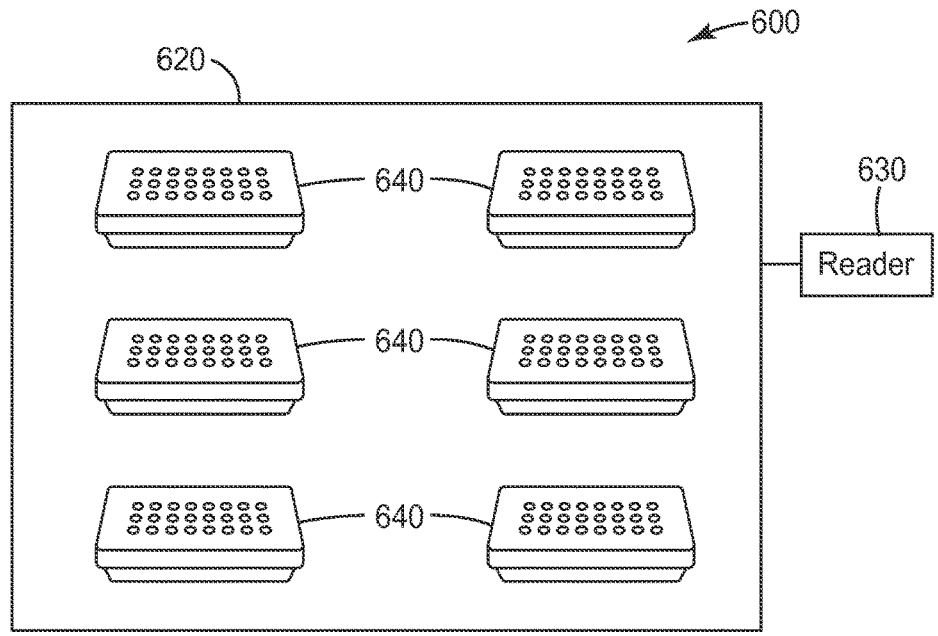

FIGS. 9B-9D illustrate another embodiment of a sensing system 600 using one or more MMR sensors disposed in a container. The MMR sensor 610B is disposed in a container 640, for example, a sterilization container. The MMR sensor 610B can be any one of the MMR sensors described in the present disclosure. As an example as illustrated in FIG. 9C, the container 640 is used for enclosing one or more surgical or medical instruments 9110 during a sterilization procedure. The container 640 may also be used to hold any other article, fluid, etc., to be sterilized prior to use in a medical procedure. The material used to construct the sterilization container is typically a metal or a metal alloy, however, any material that can survive the sterilization procedure can be utilized to construct the container 640. The material can be rigid or flexible. In some embodiments, the container material is one which allows at least partial passage of electromagnetic waves of frequencies. Containers made of conductive materials (such as aluminum) act as shields to electromagnetic waves, but the shielding is not perfect. At the frequencies of interest in the present disclosure, for example, approximately 50 kHz, and a container made of aluminum (resistivity $\rho=2.6548\mu\Omega\cdot cm$, relative permeability $\mu_r=1.000022$), the skin depth is $\delta=366.73$ μm. The attenuation through a container wall, for example, with the wall thickness d=2 mm, is $e^{-d/\delta}=4.28\times10^{-3}$. This level of attenuation allows sufficient transmission of electromagnetic waves to excite the resonance of the MMR sensor. In some embodiments, slots or holes or other openings can be cut through the wall or walls of the container 640 to allow for the transmission of electromagnetic waves in and out of the container 640. The container 640 can be of any shape and size that is suitable for enclosing its contents. In some embodiments, if the material is not permeable to electromagnetic waves, due to the composition of the material or the thickness of the material or other reasons, slots or holes or other openings can be cut through the wall or walls of the container 640 to allow for the transmission of electromagnetic waves in and out of the container 640. The container 640 can be of any shape and size that is suitable for enclosing its contents.

FIG. 9C is a view of a container 640 that is in an open configuration, into which a MMR sensor 610B and some surgical instruments 9110 are placed. In some embodiments, one or more MMR sensors can be placed at any location inside the container 640. More than one MMR sensors can be placed inside the same sterilization container. Any MMR sensor described herein can be disposed inside the container 640. In the cases of more than one MMR sensors being used, the MMR sensors can be of the same or different constructions.

FIG. 9D illustrates a sensing system 600 with one or more containers 640 disposed within an environment 620. Each container 640 can have one or more MMR sensors 610B. The sensing system 600 includes a reader 630, as described above. As an example, the reader 630 can be a frequency analyzer.

Figure 11A:
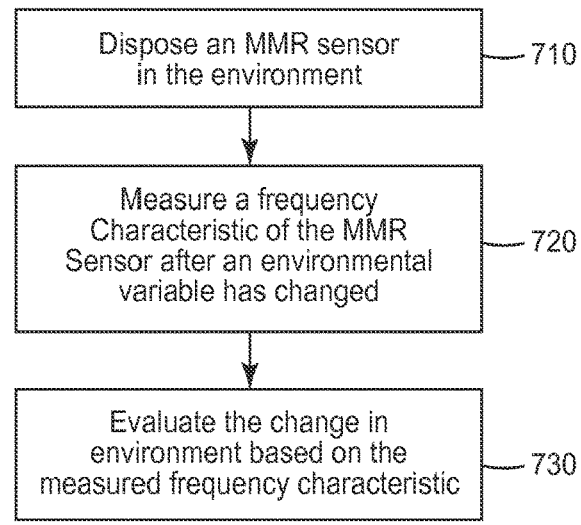
FIG. 11A illustrates a flow diagram of one embodiment of an MMR sensing system.

FIG. 11A illustrates a flow diagram of one embodiment of an MMR sensing system. First, an MMR sensor is disposed in the environment (step 710). The MMR sensor can be any one of the MMR sensors described herein. Next, an MMR reader measures a frequency characteristic of the MMR sensor after an environmental variable has changed (step 720). The system evaluates the change to the environmental variable based on the measured frequency characteristic (step 730).

Figure 11B:
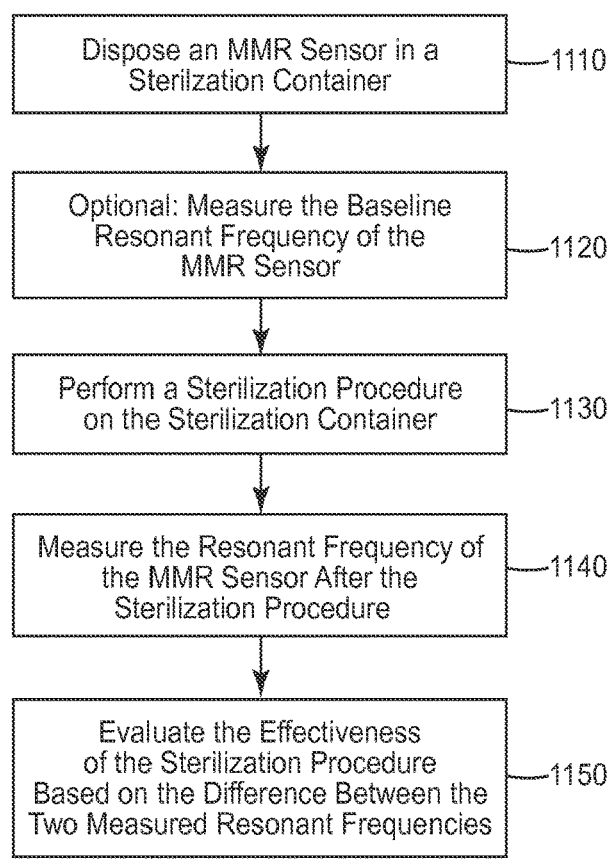
FIG. 11B illustrates a flow diagram of one embodiment of an MMR sensing system for monitoring the effectiveness of a sterilization procedure.

FIG. 11B illustrates a flow diagram of one embodiment of an MMR sensing system for monitoring the effectiveness of a sterilization procedure. One or more MMR sensors are disposed inside a sterilization container (Step 1110). Any MMR sensor described herein can be disposed inside the sterilization container, and more than one MMR sensors can be placed in the same sterilization container. In the cases of more than one MMR sensors being used, the MMR sensors can be of the same or different construction. Optionally, a reader measures the resonant frequency of the MMR sensor and this measurement can serve as the baseline resonant frequency (Step 1120). Step 1120 can be performed with the sterilization container in a closed or opened configuration. In situations where the baseline resonant frequency of the MMR sensor is known, for example, Step 1120 can be omitted. However, performing step 1120 verifies that a MMR sensor is in fact placed inside the sterilization container. Next, the sterilization container along with its contents is put through a sterilization procedure (Step 1130). After the sterilization procedure, a reader measures the resonant frequency of the MMR sensor (Step 1140). Step 1140 can be performed with the sterilization container in a closed or opened configuration. Next, a comparison is made between the baseline resonant frequency and the after sterilization resonant frequency of the MMR sensor (Step 1140). In some embodiments, a change in the resonant frequency after the sterilization procedure over a threshold may be used to indicate that the sterilization procedure was effective.

EXAMPLES

Example 1

MMR Sensor Assembly—Patterned Wicking String

With reference to FIG. 1A and modification of the environmental change receptor 140 location, MMR sensors 100 were assembled in the following manner. A channel 160 was created on first resonator major surface 132 of the resonator 130 by using a physical technique. A 3.5 cm (1.4 inches) length, 4.7E-2 cm (1.9E-2 inches) diameter wicking string obtained from Excell Mills, Inc., Mount Holly, N.C. was used to create the channel 160. The wicking string was adhered by Scotch 467MP adhesive from 3M Company, St Paul, Minn. to the long axis of the first resonator major surface 132 in the pattern described in FIG. 4B. A Metglas® 2826 MB Magnetic Alloy of dimensions 3.7 cm (1.5 inches)×6.2E-1 cm (2.4E-1 inches)×3.0E-3 mm (1.2E-3 inches), obtained from Metglas® of Conway, S.C., was selected for the resonator 130. The spacer 120 of dimensions 3.7 cm (1.5 inches)×6.2E-1 cm (2.4E-1 inches)×1.0E-2 cm (3.9E-3 inches) was constructed of Acrylonitrile Butadiene Styrene (ABS) obtained from Plastics International, Eden Prairie, Minn. The magnetic bias layer 110 commercially obtained from The Arnold Engineering Company of Marengo, Ill. as ArnoKrome™ III with dimensions×2.77 cm (1.09 inches)×6.0E-1 cm (2.4E-1 inches)×6.0E-3 cm (2.4E-3 inches) received the spacer 120. A housing 150 encapsulating the three layers, magnetic bias 110, spacer 120, and resonator 130, was constructed of Acrylonitrile Butadiene Styrene (ABS) obtained from obtained from Plastics International, Eden Prairie, Minn. The environmental change receptor 140 comprised a wax obtained from Langley/Empire Candle LLC, Kansas City, Kans. The environmental change receptor 140 was in a solid pellet form of mass 5.0 mg.

Comparative Example 1 and Example 2

MMR Sensor—Patterned Wicking String

The resonance frequency of MMR sensors assembled in Example 1 were measured by a model 4294A Precision Impedance Analyzer device with a model 16047 connector accessory both obtained from Agilent, Santa Clara, Calif. The device was calibrated by Agilent on Nov. 15, 2013. A custom MMR excitation/detection coil assembly was constructed comprising tight windings of enameled wire around a highly dielectric polyvinyl chloride (PVC) tube. The tube was constructed with a slot to receive an MMR sensor. 100 turns of #24 gauge enameled wire were wound around the 2.2 cm (7.9E-1 inches) diameter dielectric tube where the length of the winding was 5.7 cm (2.2 inches) with a measured inductance of 70.6 uH. The coil was connected to the HIGH and LOW ports of the 16047 connector accessory and the MMR sensors were placed in the custom coil assembly. A 2 mA oscillation current, swept from 57.3 kHz to 59.3 kHz measured the real and reactive impedance components of the MMR sensor. The resonant frequencies were measured (E2) and compared to the baseline (CE1). Table 1 provides an overview of MMR sensor frequency shifts when subjected to the environmental change.

TABLE 1

Patterned Wicking String

| Example | Environmental Change Receptor | Mass of Change Receptor (mg) | Location of Change Receptor | Resonant Frequency (kHz) | Resonant Frequency Shift (kHz) |
|---|---|---|---|---|---|
| CE1 | None | 5.0 | None | 59.1 | |
| E2 | Wax | 5.0 | Center of Resonator | 57.1 | 2.0 |

Example 3

MMR Sensor Assembly—Patterned Wicking Paper

With reference to FIG. 1A and modification of the environmental change receptor 140 location, MMR sensors 100 were assembled in the following manner. A channel 160 was created on first resonator major surface 132 of the resonator 130 by using a physical technique. Multiple pieces of 3.7 cm (1.5 inches)×3.6E-1 to 4.1E-1 cm (1.4E-1 to 1.6E-1 inches)× 2.0E-2 cm (7.9E-3 inches) Nexcare First Aid Gentile Paper Tape obtained from 3M Company, St. Paul, Minn. was used to create the channel 160. The wicking paper was adhered to the long axis of the first resonator major surface 132 in the pattern described in FIG. 4B. A Metglas™ 2826 MB Magnetic Alloy of dimensions 3.7 cm (1.5 inches)×6.2E-1 cm (2.4E-1 inches)×3.0E-3 cm (1.2E-3 inches), obtained from Metglas® of Conway, S.C., was selected for the resonator 130. The spacer 120 of dimensions 3.7 cm (1.5 inches)× 6.2E-1 cm (2.4E-1 inches)×1.0E-2 cm (3.9E-3 inches) was constructed of Acrylonitrile Butadiene Styrene (ABS) obtained from Plastics International, Eden Prairie, Minn. The magnetic bias layer 110 commercially obtained from The Arnold Engineering Company of Marengo, Ill. as ArnoKrome™ III with dimensions×2.77 cm (1.09 inches)× 6.0E-1 cm (2.4E-1 inches)×6.0E-3 cm (2.4E-3 inches) received the spacer 120. A housing 150 encapsulating the three layers, magnetic bias 110, spacer 120, and resonator 130, was constructed of Acrylonitrile Butadiene Styrene (ABS) obtained from obtained from Plastics International, Eden Prairie, Minn. The environmental change receptor 140 comprised a wax obtained from Langley/Empire Candle LLC, Kansas City, Kans. The environmental change receptor 140 was in a solid pellet form and range in mass from 3.0 to 7.0 mg.

Comparative Examples 2-3 and Examples 4-5

MMR Sensor—Patterned Wicking Paper

The resonance frequency of MMR sensors assembled in Example 3 were measured by a model 4294A Precision Impedance Analyzer device with a model 16047 connector accessory both obtained from Agilent, Santa Clara, Calif. The device was calibrated by Agilent on Nov. 15, 2013. A custom MMR excitation/detection coil assembly was constructed comprising tight windings of enameled wire around a highly dielectric polyvinyl chloride (PVC) tube. The tube was constructed with a slot to receive an MMR sensor. 100 turns of #24 gauge enameled wire were wound around the 2.2 cm (7.9E-1 inches) diameter dielectric tube where the length of the winding was 5.7 cm (2.2 inches) with a measured inductance of 70.6 uH. The coil was connected to the HIGH and LOW ports of the 16047 connector accessory and the MMR sensors were placed in the custom coil assembly. A 2 mA oscillation current, swept from 45 kHz to 55 kHz measured the real and reactive impedance components of the MMR sensor. The resonant frequencies were measured (E4 and E5) and compared to two baselines of the resonator and adhered tape (CE2 and CE3). Table 2 provides an overview of MMR sensor frequency shifts when subjected to the environmental change.

TABLE 2

Patterned Wicking Paper

| Example | Environmental Change Receptor | Mass of Change Receptor (mg) | Location of Change Receptor | Resonant Frequency (kHz) | Resonant Frequency Shift (kHz) |
|---|---|---|---|---|---|
| CE2 | None | None | None | 51.3 | |
| E4 | Wax | 3.5 (1.75 & 1.75) | Ends of Resonator | 52.8 | 1.5 |
| CE3 | None | None | None | 49.2 | |
| E5 | Wax | 6.3 (3.15 & 3.15) | Ends of Resonator | 51.8 | 2.6 |

Example 6

MMR Sensor Assembly—Digital Wash

With reference to FIG. 1A and modification of the environmental change receptor 140 location, MMR sensors 100 were assembled in the following manner. The resonator 130 of dimensions 3.7 cm (1.5 inches)×6.2E-1 cm (2.4E-1 inches)×3.0E-3 cm (1.2E-3 inches) commercially available as Metglas® 2826 Magnetic Alloy of Conway, S.C. The spacer 120 of dimensions 3.7 cm (1.5 inches)×6.2E-1 cm (2.4E-1 inches)×1.0E-2 cm (3.9E-3 inches) was constructed of Acrylonitrile Butadiene Styrene (ABS) obtained from Plastics International, Eden Prairie, Minn. The magnetic bias layer 110 commercially obtained from The Arnold Engineering Company of Marengo, Ill. as ArnoKrome™ III with dimensions×2.77 cm (1.09 inches)×6.0E-1 cm (2.4E-1 inches)×6.0E-3 cm (2.4E-3 inches) received the spacer 120. A housing 150 encapsulating the three layers, magnetic bias 110, spacer 120, and resonator 130, was constructed of Acrylonitrile Butadiene Styrene (ABS) obtained from obtained from Plastics International, Eden Prairie, Minn. The environmental change receptor 140 comprised 3M Soil commercially available from 3M Company, Saint Paul, Minn. in solid form with masses ranging from 3.0 to 32 mg. The environmental change receptor 140 was adhered to the long axis of the first resonator major surface 132 in the pattern described in FIG. 4D.

Comparative Example 4 and Examples 7-9

MMR Sensor—Digital Wash

Figure 12A:
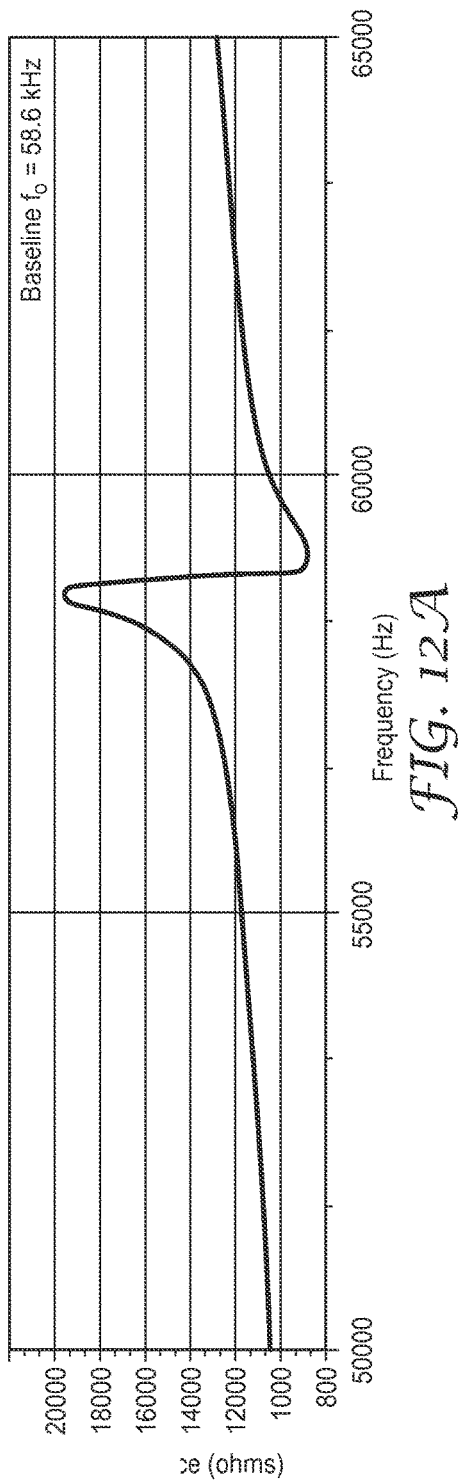
FIGS. 12A-12D are impedance versus frequency graphs of example embodiments of MMR sensors used for wash monitoring with different configurations.
Figure 12B:
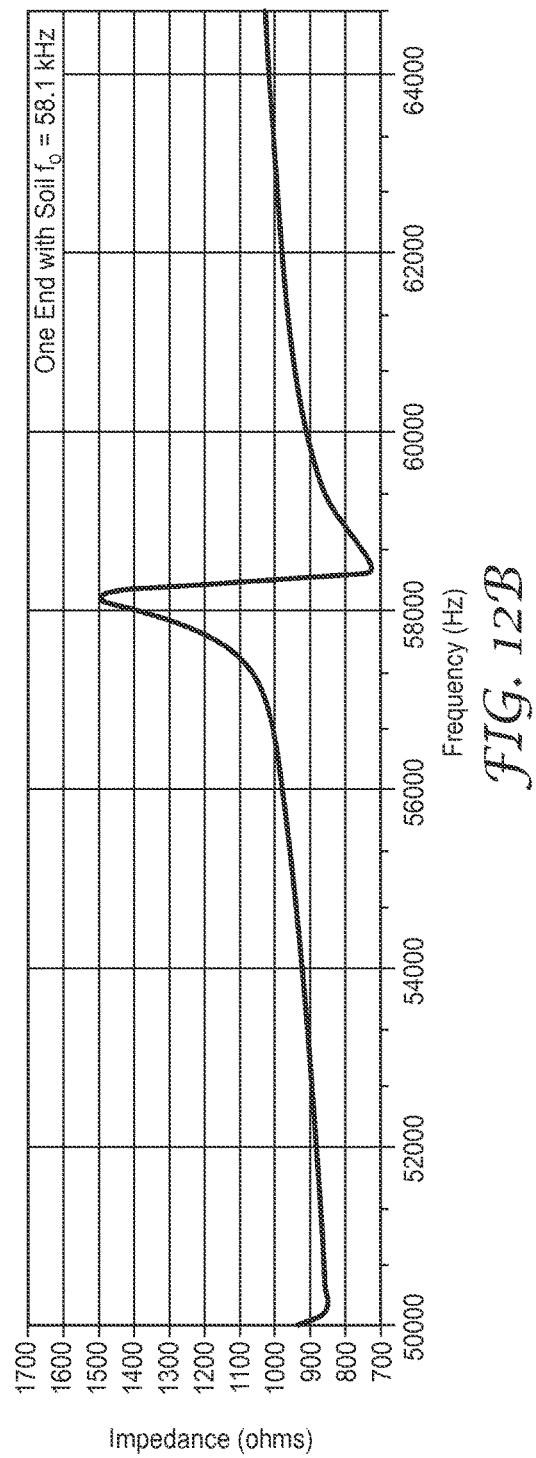
Figure 12C:
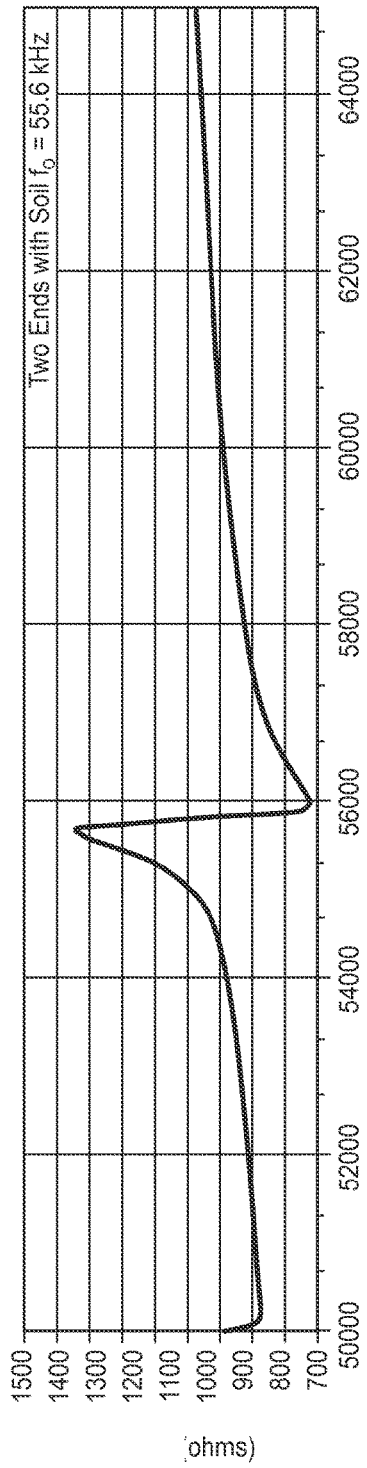
Figure 12D:

Additional MMR sensors assembled as described in Example 6 were measured by an impedance analyzer evaluation board AD5933EBZ from Analog Devices device obtained from Analog Devices, Norwood, Mass. and a wound coil of wire to record baseline resonant frequency. 100 turns of #24 gauge enameled wire were wound around a 2.2 cm (7.9E-1 inches) diameter PVC dielectric tube where the length of the winding was 4.0 cm with a measured inductance of 156.0 uH. Various masses of 3M Soil supplied by 3M Company, Saint Paul, Minn. were deposited and dried on the ends of the resonator (FIG. 8A and FIG. 8B). The MMR sensors were placed in beaker of water on hot plate with a magnetic stirrer. The MMR sensors were removed from the chamber and the resonant frequency of the MMR sensors (E10-E12) were measured and compared to the baseline (CE4). Table 3 represents the baseline and measured resonating frequencies. A successful shift in resonant frequency resulted in successful detection of instrument digital wash. FIG. 12A is a baseline representation (CE4) of the impedance versus frequency without 3M Soil. FIG. 12B illustrates (E7) the impedance versus frequency response of a resonator with 3M Soil present on one end of the resonator. FIG. 12C illustrates (E8) the impedance versus frequency response of a resonator with 3M Soil present at both ends of the resonator. FIG. 12D illustrates (E9) the impedance versus frequency response of a resonator with 3M Soil fully applied to the surface of the resonator.

TABLE 3

Digital Wash

| Example | Environmental Change Receptor | Mass of Change Receptor (mg) | Location of Change Receptor | Resonant Frequency (kHz) | Resonant Frequency Shift (kHz) |
|---|---|---|---|---|---|
| CE4 | 3M Soil | None | None | 58.6 | |
| E7 | 3M Soil | 3.3 | One End of Resonator | 58.1 | 5.0E−1 |
| E8 | 3M Soil | 6.7 (3.35 & 3.35) | Ends of Resonator | 55.6 | 3.0 |
| E9 | 3M Soil | 31.7 | Full Surface of Resonator | 54.6 | 4.0 |

Example 10

MMR Sensor Assembly—Sterilization

With reference to FIG. 1A and modification of the environmental change receptor 140 location, MMR sensors 100 were assembled in the following manner. A channel 160 was chemically coated onto the first resonator major surface 132 of the resonator 130 by using mechanically durable sintered nanosilica coatings. Nanosilica particles were applied from an aqueous dispersion and sintered by the application of heat. A channel pattern of 2.7 cm (1.1 inches)×3.0E-1 cm (1.2E-1 inches) was formed on the resonator 130 of dimensions 3.7 cm (1.5 inches)×6.2E-1 cm (2.4E-1 inches)×3.0E-3 cm (1.2E-3 inches) commercially available as Metglas® 2826 Magnetic Alloy of Conway, S.C. The coating was adhered to the long axis of the first resonator major surface 132 in the pattern described in FIG. 4B. The spacer 120 of dimensions 3.7 cm (1.5 inches)×6.2E-1 cm (2.4E-1 inches)×1.0E-2 cm (3.9E-3 inches) was constructed of Acrylonitrile Butadiene Styrene (ABS) obtained from Plastics International, Eden Prairie, Minn. The magnetic bias layer 110 commercially obtained from The Arnold Engineering Company of Marengo, Ill. as ArnoKrome™ III with dimensions×2.77 cm (1.09 inches)×6.0E-1 cm (2.4E-1 inches)×6.0E-3 cm (2.4E-3 inches) received the spacer 120. A housing 150 encapsulating the three layers, magnetic bias 110, spacer 120, and resonator 130, was constructed of Acrylonitrile Butadiene Styrene (ABS) obtained from obtained from Plastics International, Eden Prairie, Minn. The environmental change receptor 140 comprised polyethylene-co-acrylic acid (PEAA), commercially available from Sigma-Aldrich Co. LLC, St. Louis, Mo. in a bead form with masses ranging from 6.0 to 12 mg.

Comparative Example 5 and Examples 11-13

MMR Sensor—Sterilization

Figure 13C:
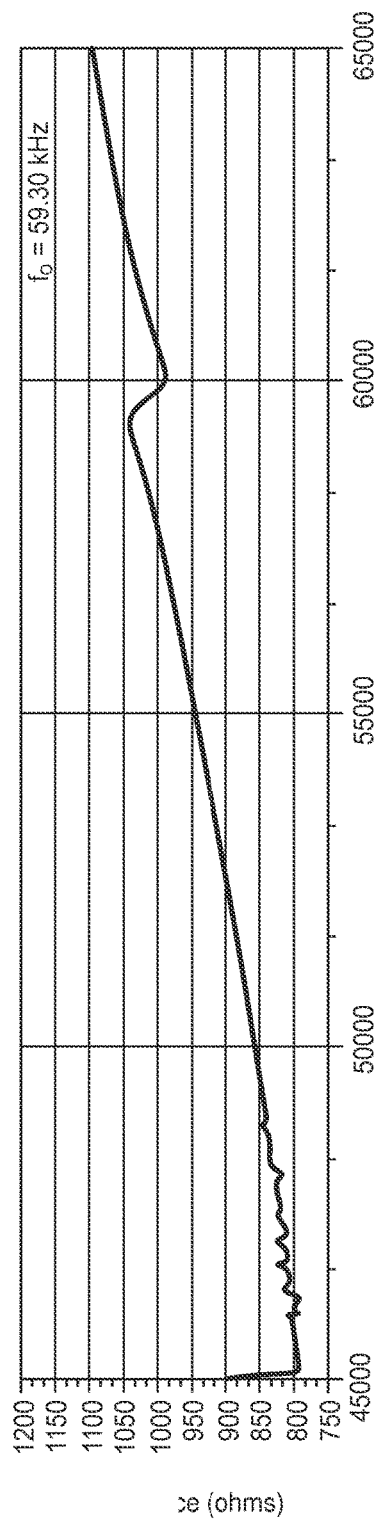
Figure 13D:
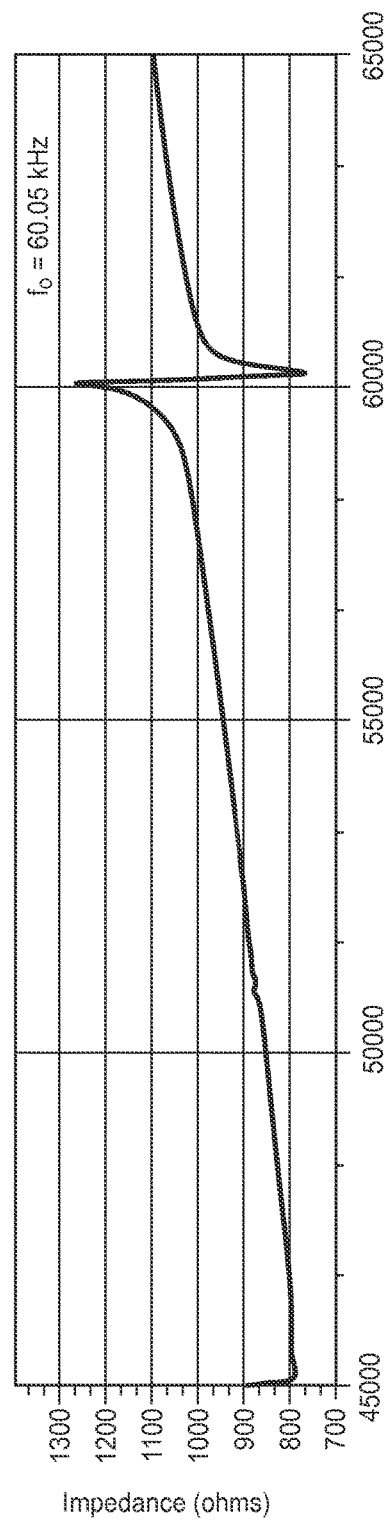

The resonance frequency of MMR sensors assembled in Example 10 were measured by a model 4294A Precision Impedance Analyzer device with a model 16047 connector accessory both obtained from Agilent, Santa Clara, Calif. The device was calibrated by Agilent on Nov. 15, 2013. A custom MMR excitation/detection coil assembly was constructed comprising tight windings of enameled wire around a highly dielectric polyvinyl chloride (PVC) tube. The tube was constructed with a slot to receive an MMR sensor. 100 turns of #24 gauge enameled wire were wound around the 2.2 cm (7.9E-1 inches) diameter dielectric tube where the length of the winding was 5.7 cm (2.2 inches) with a measured inductance of 70.6 uH. The coil was connected to the HIGH and LOW ports of the 16047 connector accessory and the MMR sensors were placed in the custom coil assembly. A 2 mA oscillation current, swept from 57.3 kHz to 59.3 kHz measured the real and reactive impedance components of the MMR sensor. Table 4 provides an overview of MMR sensor frequency shifts when subjected to the environmental change. A successful shift in resonant frequency resulted in successful detection of instrument sterilization. FIG. 13A is a baseline representation (CE5) of the impedance versus frequency of a sensor with no environmental change receptor. FIG. 13B illustrates (E11) the impedance versus frequency response of a resonator with PEAA present at the center of the resonator. FIG. 13C and FIG. 13D illustrate (E12 and E13) the impedance versus frequency response of a resonator with PEAA placed on the ends of the resonator.

TABLE 4

Sterilization Mass Distribution

| Example | Environmental Change Receptor | Mass of Change Receptor (mg) | Location of Change Receptor | Resonant Frequency (kHz) | Resonant Frequency Shift (kHz) |
|---|---|---|---|---|---|
| CE5 | None | None | None | 59.9 | |
| E11 | Polyethylene-co-Acrylic Acid | 11 | Center of Resonator | 55.0 | 4.9 |
| E12 | Polyethylene-co-Acrylic Acid | 13.8 (6.9 & 6.9) | Ends of Resonator | 59.3 | 6.0E-1 |
| E13 | Polyethylene-co Acrylic Acid | 13.8 (7.1 & 6.9) | Ends of Resonator | 60.1 | 2.0E-1 |

The MMR sensors were placed in a Getinge Steam Sterilizer, Model 666AC1, obtained from Getinge Group, Rochester, N.Y., and cycled five times to 130° C. with house steam. The resonant frequency was measured (E14) and compared to the baseline (CE6). Table 5 provides an overview of MMR sensor frequency shift with PEAA environmental change receptor mass at the center prior to sterilization (CE6) and the response of the resonator after sterilization (E14). A 1.4 kHz frequency shift is noted as the PEAA flows out from center to the ends along a predefined path.

TABLE 5

Sterilization

| Example | Environmental Change Receptor | Mass of Change Receptor (mg) | Location of Change Receptor | Resonant Frequency (kHz) | Resonant Frequency Shift (kHz) |
|---|---|---|---|---|---|
| CE6 | Polyethylene-co-Acrylic Acid | 11 | Center of Resonator | 59.74 | |

TABLE 5-continued

Sterilization

| Example | Environmental Change Receptor | Mass of Change Receptor (mg) | Location of Change Receptor | Resonant Frequency (kHz) | Resonant Frequency Shift (kHz) |
|---|---|---|---|---|---|
| E14 | Polyethylene-co Acrylic Acid | 11 | Distributed from Center of Resonator | 58.32 | 1.4 |

Example 15

MMR Sensor—Wetness Detection

Additional MMR sensors assembled as described in Example 10 were measured by a impedance analyzer evaluation board AD5933EBZ from Analog Devices device obtained from Analog Devices, Norwood, Mass. and a wound coil of wire to record baseline resonant frequency. 100 turns of #24 gauge enameled wire were wound around a 2.2 cm (7.9E-1 inches) diameter PVC dielectric tube where the length of the winding was 4.0 cm (1.6 inches) with a measured inductance of 156.0 uH. A double chamber package design of FIG. 7A was used with two sets of venting slots in the removable plastic cover. A bias magnet was glued to the top of the bottom chamber and a Metglas® 2826 MB second resonator to indicate presence was placed to freely oscillate in the bottom chamber, and the chamber sealed with a permanent film seal. In the top chamber, an expandable 3M Scotch-Brite™ Greener Clean biodegradable expanding soft sponge was placed in the chamber and a Metglas® 2826 MB resonator was placed on top of the sponge. As shown in the impedance versus frequency relationship in FIG. 14A, a baseline frequency $f_{dry}$ was measured. A Tuberkulin syringe was then used to apply of 0.05 ml of water to each set of vents. After application of the 0.1 ml of water a second measurement for the resonant frequency shift was performed. $F_{presence}$ in FIG. 14A and FIG. 14B represent the shift in resonant frequency.

Example 16

MMR Sensor Assembly—Gas Detection

An MMR sensor capable of detecting natural gas was assembled according to FIG. 1A with modification of the environmental change receptor 140 location. In the embodiment illustrated, the MMR sensor includes a ArnoKrome™ III magnetic bias layer 110 obtained from The Arnold Engineering Company of Marengo, Ill., a spacer 120, a resonator 130, an environmental change receptor 140, and an optional housing 150. The resonator 130 was a Vitrovac 4613 magnetic alloy from Vacuumschmelze GMBH, Hanau, Germany. The environmental change receptor 140 was Zeolite HiSiv 3000 powder from UOP LLC, Des Plaines, Ill. which was affixed to the resonator by Scotch 467MP adhesive from 3M Company, St Paul, Minn. Environmental change receptors were adhered to the long axis of the first resonator major surface 132 in the pattern described in FIG. 4D. The magnetic bias layer 110 was 3.9 cm (1.5 inches)× 1.2 cm (4.7E-1 inches)×6.0E-3 cm (2.3E-3 inches), spacer 120 was 3.9 cm (1.5 inches)×1.2 cm (4.7E-1 inches)×2.0E-1 cm (7.9E-2 inches), and resonator 130 was 4.4 cm (1.7 inches)×1.2 cm (4.7E-1 inches)×2.5E-3 cm (9.8E-4 inches).

Figure 15:
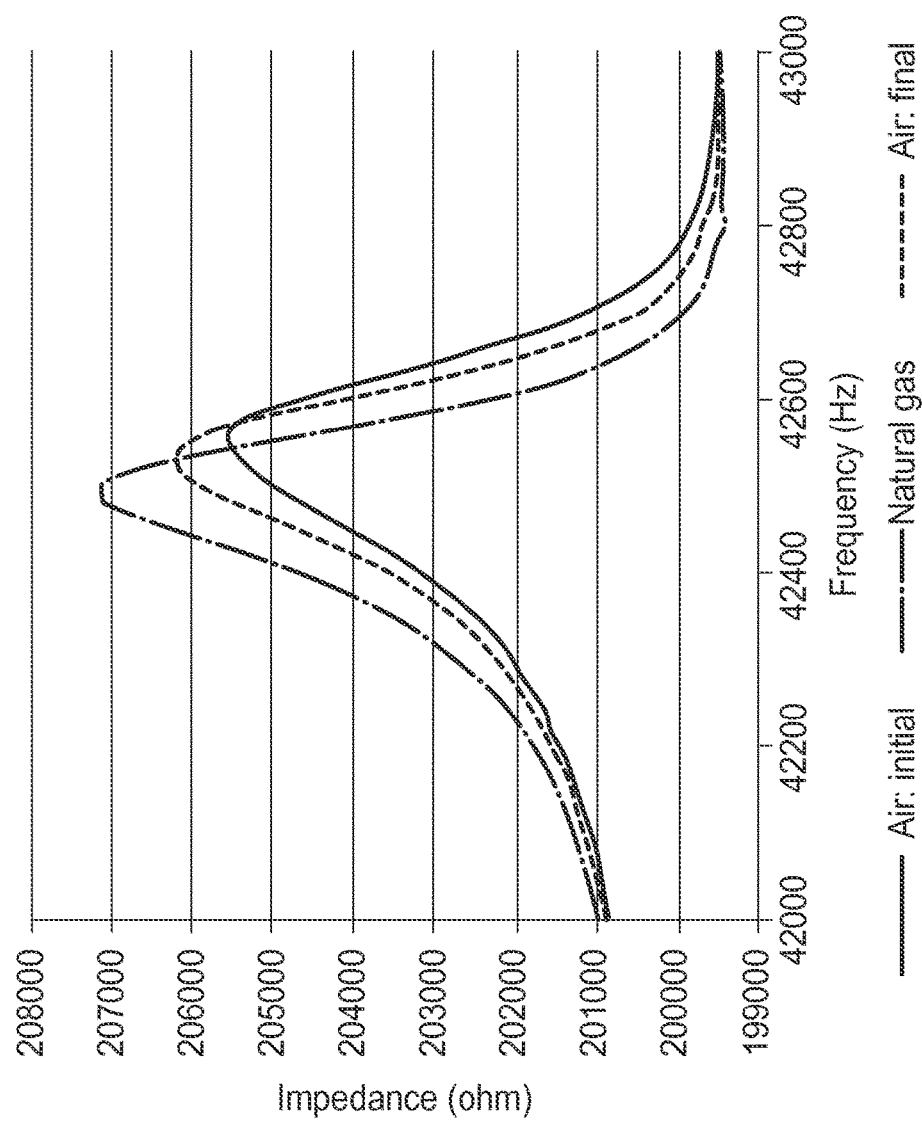
FIG. 15 illustrates impedance versus frequency graphs of example embodiments of MMR sensors used for gas detection with different configurations.

An MMR sensor was placed in a 100 turn, 5.3 cm (2.1 inches) cylindrical solenoid which was driven by an impedance analyzer evaluation board AD5933EBZ from Analog Devices, Norwood, Mass. Resonance can be defined as the frequency where the impedance is maximum, or alternatively where the phase of the impedance passes through zero. Next the MMR sensor and the measurement solenoid were placed inside a chamber through which natural gas can flow. FIG. 15 represents the impedance vs. frequency as the chamber is cycled through various conditions: (1) open to lab ambient (approximately 20° C. and 30% Relative Humidity), (2) closed with constant flow of 100% natural gas, and (3) open again to the lab ambient. The data demonstrated that the MMR sensor responds reversibly to immersion in natural gas with a shift in resonance frequency of 50 Hz.

Example 17

MMR Sensor Assembly—Sterilization with Microreplicated Film Channels on Resonator With reference to FIG. 1A and modification of the environmental change receptor 140 location, MMR sensors 100 were assembled in the following manner. A channel 160 was created physically on the first resonator major surface 132 of the resonator 130 by adhering a piece of microreplicated film (18 microns channel spacing in these examples), available from 3M. A piece of film of 2.7 cm (1.1 inches)×3.0E-1 cm (1.2E-1 inches) was adhered to the resonator 130 of dimensions 3.7 cm (1.5 inches)×6.2E-1 cm (2.4E-1 inches)×3.0E-3 cm (1.2E-3 inches) commercially available as Metglas® 2826 Magnetic Alloy of Conway, S.C. The film was adhered to the long axis of the first resonator major surface 132 using VHB™ adhesive (3M Company), with microreplicated channels flowing along the long axis. The spacer 120 of dimensions 3.7 cm (1.5 inches)×6.2E-1 cm (2.4E-1 inches)×1.0E-2 cm (3.9E-3 inches) was constructed of Acrylonitrile Butadiene Styrene (ABS) obtained from Plastics International, Eden Prairie, Minn. The magnetic bias layer 110 commercially obtained from The Arnold Engineering Company of Marengo, Ill. as ArnoKrome™ III with dimensions×2.77 cm (1.09 inches)×6.0E-1 cm (2.4E-1 inches)×6.0E-3 cm (2.4E-3 inches) received the spacer 120. A housing 150 encapsulating the three layers, magnetic bias 110, spacer 120, and resonator 130, was constructed of Acrylonitrile Butadiene Styrene (ABS) obtained from obtained from Plastics International, Eden Prairie, Minn. The environmental change receptor 140 comprised salicylamide pieces, commercially available from a number of sources such as Sigma Aldrich, St. Louis, Mo. The salicylamide was applied with masses ranging from 6.0 to 30 mg. The salicylamide was adhered to the film with VHB™ adhesive, available from 3M Company.

The resonance frequency of MMR sensors assembled in this example were measured by a model 4294A Precision Impedance Analyzer device with a model 16047 connector accessory both obtained from Agilent, Santa Clara, Calif. The device was calibrated by Agilent on Nov. 15, 2013. A custom MMR excitation/detection coil assembly was constructed comprising tight windings of enameled wire around a highly dielectric polyvinyl chloride (PVC) tube. The tube was constructed with a slot to receive an MMR sensor. 100 turns of #24 gauge enameled wire were wound around the 2.2 cm (7.9E-1 inches) diameter dielectric tube where the length of the winding was 5.7 cm (2.2 inches) with a measured inductance of 70.6 uH. The coil was connected to the HIGH and LOW ports of the 16047 connector accessory and the MMR sensors were placed in the custom coil assembly. A 2 mA oscillation current measured the real and reactive impedance components of the MMR sensor. The MMR sensors were placed in a Getinge Steam Sterilizer, Model 666AC1, obtained from Getinge Group, Rochester, N.Y., and cycled five times to 130° C. with house steam. Table 6 provides an overview of MMR sensor frequency shift with salicylamide environmental change receptor mass on microreplicated film channels on the resonator, before and after the sterilization process. Three examples are shown for the construction where the salicylamide environmental change receptor mass is located at both ends of the film/resonator prior to sterilization. Frequency shifts of 5.397, 3.27 and 6.053 kHz are noted after flow of the salicylamide towards the center due to environmental changes during sterilization. One example is shown where the salicylamide environmental change receptor mass is located at the center prior to sterilization. A 1.131 kHz frequency shift is noted as the salicylamide flows out from center to the ends along a predefined path.

TABLE 6

| Construction | Total Solicylamide Mass | Resonant Frequency before Sterilization (kHz) | Resonant Frequency after Sterilization (kHz) | Resonant Frequency Shift (kHz) |
|---|---|---|---|---|
| Resonator with microreplicated film channels, salicylamide located at both ends | 0.0173 | 48.1 | 53.497 | 5.397 |
| Resonator with microreplicated film channels, salicylamide located at both ends | 0.0231 | 47.9 | 51.17 | 3.27 |
| Resonator with microreplicated film channels, salicylamide located at both ends, with ABS housing | 0.0158 | 48.5 | 54.553 | 6.053 |
| Resonator with microreplicated film channels, salicylamide located at the center | 0.0111 | 54.783 | 55.914 | 1.131 |

Exemplary Embodiments

Embodiment A1. A sensing device, comprising:
a magnetic bias layer having a first magnetic surface and an opposing second magnetic surface, the magnetic bias layer comprising a first magnetic material,
a resonator having a first resonator major surface and an opposing second resonator major surface, the resonator comprising a second magnetic material, the second resonator major surface facing toward the first magnetic surface, the first resonator major surface having a predefined channel,
a spacer disposed between the magnetic bias layer and the resonator, and an environmental change receptor disposed proximate to the predefined channel.

Embodiment A2. The sensing device of Embodiment A1, wherein the environmental change receptor distributes along at least part of the predefined channel in response to a change in environment.

Embodiment A3. The sensing device of Embodiment A2, wherein resonant frequency of the resonator shifts in response to the distribution of the environmental change receptor along at least part of the predefined channel.

Embodiment A4. The sensing device of Embodiment A1-A3, wherein the predefined channel comprises a thin layer of material disposed on the first resonator major surface.

Embodiment A5. The sensing device of Embodiment A1-A4, wherein the predefined channel comprises a pattern on the first resonator major surface.

Embodiment A6. The sensing device of Embodiment A1-A5, wherein the predefined channel comprises a thin layer of material disposed on the first resonator major surface according to a path.

Embodiment A7. The sensing device of Embodiment A1-A6, wherein the predefined channel comprises a thin layer of material disposed proximate to a perimeter of a path.

Embodiment A8. The sensing device of Embodiment A4, wherein the thin layer of material comprises at least one of a hydrophilic material, a wicking material, a hydrophobic material, an oleophobic material, and an oleophilic material.

Embodiment A9. The sensing device of Embodiment A4, wherein the thin layer of material has a chemical reaction with the second magnetic material.

Embodiment A10. The sensor device of Embodiment A1-A9, wherein the predefined channel comprises an elongate channel across the first resonator major surface.

Embodiment A11. The sensing device of Embodiment A1-A10, wherein the predefined channel comprises one or more sections.

Embodiment A12. The sensing device of Embodiment A11, wherein at least one of the one or more sections is disposed proximate an edge of the first resonator major surface.

Embodiment A13. The sensing device of Embodiment A1-A12, wherein the environmental change receptor is disposed proximate to the center of the predefined channel.

Embodiment A14. The sensing device of Embodiment A1-A13, wherein the environmental change receptor is disposed proximate to an end of the predefined channel.

Embodiment A15. The sensing device of Embodiment A1-A14, wherein the environmental change receptor is comprises a material sensitive to temperature, moisture, liquid, gas, biological substance, chemical substance, or a combination thereof.

Embodiment A16. The sensing device of Embodiment A1-A15, further comprising:
a housing, wherein the magnetic bias layer, the resonator, and the spacer are disposed in the housing.

Embodiment A17. The sensing device of Embodiment A16, wherein the housing comprising one or more openings to allow fluid distribution into the housing.

Embodiment A18. The sensing device of Embodiment A16, wherein the housing has a plurality of chambers.

Embodiment A19. The sensing device of Embodiment A18, wherein the magnetic bias layer and the resonator are disposed in a different chamber from each other.

Embodiment A20. The sensing device of Embodiment A1-A19, further comprising: a second resonator disposed adjacent to the magnetic bias layer.

Embodiment A21. The sensing device of Embodiment A18, further comprising: a second resonator, wherein the plurality of chambers comprises a first chamber and a second chamber different from the first chamber, wherein the second resonator is disposed in the second chamber, and wherein the resonator is disposed in the first chamber.

Embodiment A22. A sensing device, comprising:
a magnetic bias layer having a first magnetic surface and an opposing second magnetic surface, the magnetic bias layer comprising a first magnetic material,
a resonator having a first resonator major surface and an opposing second resonator major surface, the resonator comprising a second magnetic material, the second resonator major surface facing toward the first magnetic surface, the first resonator major surface having a predefined channel,
a spacer disposed between the magnetic bias layer and the resonator,
an environmental change receptor disposed proximate to the predefined channel, and
a housing with one or more openings, containing the magnetic bias layer, the resonator, and the spacer.

Embodiment A23. A sensing device, comprising:
a magnetic bias layer having a first magnetic surface and an opposing second magnetic surface, the magnetic bias layer comprising a first magnetic material,
a resonator having a first resonator major surface and an opposing second resonator major surface, the resonator comprising a second magnetic material, the second resonator major surface facing toward the first magnetic surface, the first resonator major surface having a predefined channel,
an environmental change receptor disposed proximate to the predefined channel, and
a housing containing the magnetic bias layer, the resonator, and a supporting structure to support the resonator.

Embodiment B1. A sensing device, comprising:
a magnetic bias layer having a first magnetic surface and an opposing second magnetic surface, the magnetic bias layer comprising a first electromagnetic material,
a resonator having a first resonator major surface and an opposing second resonator major surface, the resonator comprising a second magnetic material, the second resonator major surface facing toward the first magnetic surface,
a spacer disposed between the magnetic bias layer and the resonator, and
an environmental change receptor disposed on the first resonator major surface,
wherein the mass of the environmental change receptor is changed in response to a change in environment,
wherein resonant frequency of the sensing device shifts in response to the mass change of the environmental change receptor.

Embodiment B2. The sensing device of Embodiment B1, wherein the first resonator major surface has a predefined channel, wherein the environmental change receptor is disposed on at least part of the predefined channel.

Embodiment B3. The sensing device of Embodiment B1-B2, wherein the predefined channel comprises a thin layer of material disposed on the first resonator major surface.

Embodiment B4. The sensing device of Embodiment B1-B3, wherein the environmental change receptor is comprises a material sensitive to temperature, moisture, gas, or a combination thereof.

Embodiment B5. The sensing device of Embodiment B1-B4, wherein at least part of the environmental change receptor is disposed proximate to an edge of the first resonator major surface.

Embodiment B6. The sensing device of Embodiment B1-B5, wherein the mass of the environmental change receptor is increased.

Embodiment B7. The sensing device of Embodiment B1-B6, wherein the mass of the environmental change receptor is reduced.

Embodiment B8. The sensing device of Embodiment B1-B7, wherein the environmental change receptor includes a plurality of receptor elements.

Embodiment B9. The sensing device of Embodiment B8, wherein at least part of the plurality of receptor elements are disposed in a pattern.

Embodiment B10. The sensing device of Embodiment B1-B9, further comprising: a housing, wherein the magnetic bias layer, the resonator, and the spacer are disposed in the housing.

Embodiment B11. The sensing device of Embodiment B10, wherein the housing comprising one or more openings to allow fluid distribution into the housing.

Embodiment B12. The sensing device of Embodiment B10, wherein the housing has a plurality of chambers.

Embodiment B13. The sensing device of Embodiment B12, wherein the magnetic bias layer and the resonator are disposed in a different chamber from each other.

Embodiment B14. The sensing device of Embodiment B1-B13, further comprising: a second resonator disposed adjacent to the magnetic bias layer.

Embodiment B15. The sensing device of Embodiment B12, further comprising: a second resonator, wherein the plurality of chambers comprises a first chamber and a second chamber different from the first chamber, wherein the second resonator is disposed in the second chamber, and wherein the resonator is disposed in the first chamber.

Embodiment B16. A sensing device, comprising: a magnetic bias layer having a first magnetic surface and an opposing second magnetic surface, the magnetic bias layer comprising a first magnetic material,
 a resonator having a first resonator major surface and an opposing second resonator major surface, the resonator comprising a second magnetic material, the second resonator major surface facing toward the first magnetic surface,
 a spacer disposed between the magnetic bias layer and the resonator,
 an environmental change receptor disposed on the first resonator surface, and
 a housing with one or more openings, wherein the magnetic bias layer, the resonator, and the spacer are disposed in the housing.

Embodiment B17. The sensing device of Embodiment B16, wherein the mass of the environmental change receptor is changed in response to a change in environment, and wherein resonant frequency of the sensing device shifts in response to the mass change of the environmental change receptor.

Embodiment B18. The sensing device of Embodiment B16, wherein the environmental change receptor comprises a plurality of receptor elements, wherein at least one of the plurality of receptor elements is disposed proximate to an end of the resonator.

Embodiment B19. A sensing device, comprising:
 a magnetic bias layer having a first magnetic surface and an opposing second magnetic surface, the magnetic bias layer comprising a first magnetic material,
 a resonator having a first resonator major surface and an opposing second resonator major surface, the resonator comprising a second magnetic material, the second resonator major surface facing toward the first magnetic surface,
 an environmental change receptor disposed on the first magnetic surface, and
 a housing comprising a supporting structure to support the resonator, wherein the magnetic bias layer and the resonator are disposed in the housing.

Embodiment B20. The sensing device of Embodiment B19, wherein the environmental change receptor comprises a plurality of receptor elements, wherein at least one of the plurality of receptor elements is disposed proximate to an end of the resonator.

Embodiment C1. A system for sensing a change in environment, comprising:
 a MMR sensor configured to be disposed in the environment, the MMR sensor comprising:
 a magnetic bias layer having a first magnetic surface and an opposing second magnetic surface, the magnetic bias layer comprising a first electromagnetic material,
 a resonator having a first resonator major surface and an opposing second resonator major surface, the resonator comprising a second magnetic material, the second resonator major surface facing toward the first magnetic surface,
 a spacer disposed between the magnetic bias layer and the resonator, and
 an environmental change receptor disposed proximate to the first resonator major surface,
 wherein a property of the environmental change receptor changes in response to a change to an environmental variable and thereby changes resonant frequency of the MMR sensor;
 a reader configured to measure a after-change frequency characteristic of the MMR sensor after the environmental variable changes, wherein the change to the environmental variable is evaluated based on the after-change frequency characteristic.

Embodiment C2. The system of Embodiment C1, wherein the reader is further configured to measure a before-change frequency characteristic of the MMR sensor before the environmental variable changes, and wherein the change to the environmental variable is evaluated based on the before-change frequency characteristic and the after-change frequency characteristic.

Embodiment C3. The system of Embodiment C1-C2, wherein the reader comprises at least one of an acoustic detection device, and a swept frequency oscillator.

Embodiment C4. The system of Embodiment C1-C3, wherein the first resonator major surface has a predefined channel, wherein the environmental change receptor comprises an environmentally responsive material before the change in environment, and wherein the environmentally responsive material is distributed along at least a portion of the predefined channel when the environmental variable changes.

Embodiment C5. The system of Embodiment C1-C4, wherein the environmental change receptor is disposed on at least a portion of the first resonator major surface before the environmental variable changes, and wherein the mass of the environmental change receptor disposed on the first resonator major surface is changed in response to the change to the environmental variable.

Embodiment C6. The system of Embodiment C5, wherein the environmental change receptor includes a plurality of receptor elements.

Embodiment C7. The system of Embodiment C1-C6, wherein the environmental variable is temperature.

Embodiment C8. The system of Embodiment C7, wherein the environmental change receptor comprises a meltable material.

Embodiment C9. The system of Embodiment C1-C8, wherein the environmental element is humidity.

Embodiment C10. The system of Embodiment C9, wherein the environmental change receptor comprises a porous material.

Embodiment C11. A system for sensing a change in environment, comprising:
  a first MMR sensor and a second MMR sensor disposed in the environment, each of the first and the second MMR sensors comprising:
  a magnetic bias layer having a first magnetic surface and an opposing second magnetic surface, the magnetic bias layer comprising a first electromagnetic material,
  a resonator having a first resonator major surface and an opposing second resonator major surface, the resonator comprising a second magnetic material, the second resonator major surface facing toward the first magnetic surface,
  a spacer disposed between the magnetic bias layer and the resonator, and
  an environmental change receptor disposed proximate to the first resonator major surface,
  wherein a property of the environmental change receptor changes in response to a change to an environmental variable and thereby changes resonant frequency of the respective MMR sensor;
  a reader configured to measure a after-change frequency characteristic of the MMR sensors after the change to the environmental variable, wherein the change to the environmental variable is evaluated based on the after-change frequency characteristic.

Embodiment C12. The system of Embodiment C11, wherein the resonator of the first MMR sensor is different in dimension from the resonator of the second MMR sensor.

Embodiment C13. The system of Embodiment C11-C12, wherein each of the first MMR sensor and the second MMR sensor has a predefined channel on its respective first resonator major surface.

Embodiment C14. A system for sensing a change in environment, comprising:
  a container disposed in the environment, the container configured to store one or more articles,
  an MMR sensor disposed in the container, the MMR sensors comprising:
    a housing,
    a magnetic bias layer having a first magnetic surface and an opposing second magnetic surface, the magnetic bias layer comprising a first electromagnetic material,
    a resonator having a first resonator major surface and an opposing second resonator major surface, the resonator comprising a second magnetic material, the second resonator major surface facing toward the first magnetic surface,
    a spacer disposed between the magnetic bias layer and the resonator, and
    an environmental change receptor disposed proximate to the first resonator major surface,
  wherein the magnetic bias layer, the resonator, the spacer, and the environmental change receptor are disposed in the housing
  wherein a property of the environmental change receptor changes in response to a change to an environmental variable and thereby changes resonant frequency of the MMR sensor;
  a reader configured to measure a after-change frequency characteristic of the first and the second MMR sensors after the change to the environmental variable, wherein the change to the environmental variable is evaluated based on the after-change frequency characteristic.

Embodiment C15. The system of Embodiment C14, wherein the MMR sensor further comprising: a predefined channel disposed on the first resonator major surface.

Embodiment C16. The system of Embodiment C15, wherein the environmental change receptor distributes along at least part of the predefined channel in response to the change to the environmental variable.

Embodiment C17. The system of Embodiment C14-C16, wherein the environmental change receptor is an integrated part of the spacer.

Embodiment C18. The system of Embodiment C14-C17, wherein the reader is further configured to measure a before-change frequency characteristic of the MMR sensor before the environmental variable changes, and wherein the change to the environmental variable is evaluated based on the before-change frequency characteristic and the after-change frequency characteristic.

Embodiment C19. A system for sensing a change in environment, comprising:
  a plurality of containers disposed in the environment, each container configured to store one or more articles,
  a plurality of MMR sensor disposed in the plurality of containers, each MMR sensors comprising:
    a housing,
    a magnetic bias layer having a first magnetic surface and an opposing second magnetic surface, the magnetic bias layer comprising a first electromagnetic material,
    a resonator having a first resonator major surface and an opposing second resonator major surface, the resonator comprising a second magnetic material, the second resonator major surface facing toward the first magnetic surface,
    a spacer disposed between the magnetic bias layer and the resonator, and
    an environmental change receptor disposed proximate to the first resonator major surface,
  wherein the magnetic bias layer, the resonator, the spacer, and the environmental change receptor are disposed in the housing
  wherein a property of the environmental change receptor changes in response to a change to an environmental variable and thereby changes resonant frequency of the MMR sensor;
  a reader configured to measure a after-change frequency characteristic of at least some of the plurality of sensors after the change to the environmental variable.

Embodiment C20. The system of Embodiment C19, wherein the reader is further configured to measure a before-change frequency characteristic of at least one of the plurality of MMR sensors before the environmental variable changes.

Embodiment C21. The system of Embodiment C19-C20, wherein each of the plurality of MMR sensors further comprising: a predefined channel disposed on the first resonator major surface.

Embodiment C22. The system of Embodiment C21, wherein the environmental change receptor distributes along at least part of the predefined channel in response to the change to the environmental variable.

Embodiment C23. The system of Embodiment C19-C22, wherein the resonators of at least two of the plurality of MMR sensors have different dimensions.

Embodiment C24. A method for detecting a change in environment, comprising:
  disposing a MMR sensor in the environment, the MMR sensor comprising:
    a magnetic bias layer having a first magnetic surface and an opposing second magnetic surface, the magnetic bias layer comprising a first electromagnetic material,
    a resonator having a first resonator major surface and an opposing second resonator major surface, the resonator comprising a second magnetic material, the second resonator major surface facing toward the first magnetic surface,
    a spacer disposed between the magnetic bias layer and the resonator, and
    an environmental change receptor disposed proximate to the first resonator major surface,
    wherein a property of the environmental change receptor changes in response to a change to an environmental variable and thereby changes resonant frequency of the MMR sensor;
  subjecting the MMR sensor to a change to an environmental variable;
  measuring an after-change frequency characteristic of the MMR sensor;
  evaluating the change to the environmental variable based on the after-change frequency characteristic.

Embodiment C25. The method of Embodiment C24, further comprising:
  measuring a before-change frequency characteristic of the MMR sensor before the change to the environmental variable; and
  evaluating the change to the environmental variable based on the before-change frequency characteristic and the after-change frequency characteristic.

Embodiment C26. The method of Embodiment C24-C25, wherein the first resonator major surface has a predefined channel, wherein the environmental change receptor comprises an environmentally responsive material before the change in environment, and wherein the environmentally responsive material is distributed along at least a portion of the predefined channel when the environmental variable changes.

Embodiment C27. The method of Embodiment C24-C26, wherein the environmental change receptor is disposed on at least a portion of the first resonator major surface before the environmental variable changes, and wherein the mass of the environmental change receptor disposed on the first resonator major surface is changed in response to the change to the environmental variable.

Embodiment C28. The method of Embodiment C27, wherein the environmental change receptor includes a plurality of receptor elements.

Embodiment C29. The method of Embodiment C28, wherein at least one of the plurality of receptor elements is disposed proximate to an edge of the resonator.

Embodiment C30. The method of Embodiment C24-C29, wherein the environmental change receptor comprises a meltable material.

Embodiment C31. The method of Embodiment C24-C30, wherein the environmental change receptor comprises a porous material.

Embodiment D1. A sensing device, comprising:
  a magnetic bias layer having a first magnetic surface and an opposing second magnetic surface, the magnetic bias layer comprising a first electromagnetic material,
  a resonator having a first resonator major surface and an opposing second resonator major surface, the resonator comprising a second magnetic material, the second resonator major surface facing toward the first magnetic surface,
  a spacer, and
  a housing containing the magnetic bias layer, the resonator, and the spacer,
  wherein the spacer comprises an environmental change receptor,
  wherein the thickness of the environmental change receptor rapidly increases in response to a change to an environment variable.

Embodiment D2. The sensing device of Embodiment D1, wherein at least part of the spacer is disposed between the resonator and the magnetic bias layer.

Embodiment D3. The sensing device of Embodiment D1-D2, wherein at least part of the spacer is disposed on top of the resonator.

Embodiment D4. The sensing device of Embodiment D1-D3, wherein resonant frequency of the resonator shifts in response to the thickness change to the environmental change receptor.

Embodiment D5. The sensing device of Embodiment D1-D4, wherein the resonator is damped in response to the thickness change to the environmental change receptor.

Embodiment D6. The sensing device of Embodiment D1-D5, wherein the environmental change receptor comprises a porous material.

Embodiment D7. The sensing device of Embodiment D1-D6, wherein the environmental change receptor comprises an absorption material.

Embodiment D8. The sensing device of Embodiment D1-D7, wherein the environmental change receptor includes a plurality of receptor elements.

Embodiment D9. The sensing device of Embodiment D8, wherein at least one of the plurality of receptor elements is disposed between the resonator and the magnetic bias layer.

Embodiment D10. The sensing device of Embodiment D1-D9, further comprising: a housing, wherein the magnetic bias layer, the resonator, and the spacer are disposed in the housing.

Embodiment D11. The sensing device of Embodiment D10, wherein the housing comprising one or more openings to allow fluid distribution into the housing.

Embodiment D12. The sensing device of Embodiment D10-D11, wherein the housing has a plurality of chambers.

Embodiment D13. The sensing device of Embodiment D12, wherein the magnetic bias layer and the resonator are disposed in a different chamber from each other.

Embodiment D14. The sensing device of Embodiment D1-D13, further comprising:
  a second resonator disposed adjacent to the magnetic bias layer.

Embodiment D15. The sensing device of Embodiment D12, further comprising: a second resonator, wherein the plurality of chambers comprises a first chamber and a second chamber different from the first chamber, wherein the second resonator is disposed in the second chamber, and wherein the resonator is disposed in the first chamber.

Embodiment D16. A sensing device, comprising:
- a magnetic bias layer having a first magnetic surface and an opposing second magnetic surface, the magnetic bias layer comprising a first magnetic material,
- a resonator having a first resonator major surface and an opposing second resonator major surface, the resonator comprising a second magnetic material, the second resonator major surface facing toward the first magnetic surface,
- a spacer disposed between the magnetic bias layer and the resonator, wherein the spacer comprises an environmental change receptor, and
- a housing with one or more openings, wherein the magnetic bias layer, the resonator, and the spacer are disposed in the housing.
- wherein the thickness of the environmental change receptor rapidly increases in response to a change to an environment variable.

Embodiment D17. The sensing device of Embodiment D16, wherein at least part of the spacer is disposed between the resonator and the magnetic bias layer.

Embodiment D18. The sensing device of Embodiment D16-D17, wherein at least part of the spacer is disposed on top of the resonator.

Embodiment D19. The sensing device of Embodiment D16-D18, wherein resonant frequency of the resonator shifts in response to the thickness change to the environmental change receptor.

Embodiment D20. The sensing device of Embodiment D16-D19, wherein the resonator is damped in response to the thickness change to the environmental change receptor.

The present invention should not be considered limited to the particular examples and embodiments described above, as such embodiments are described in detail to facilitate explanation of various aspects of the invention. Rather the present invention should be understood to cover all aspects of the invention, including various modifications, equivalent processes, and alternative devices falling within the spirit and scope of the invention as defined by the appended claims and their equivalents.

What is claimed is:

1. A sensing device, comprising:
- a magnetic bias layer having a first magnetic surface and an opposing second magnetic surface, the magnetic bias layer comprising a first magnetic material,
- a resonator having a first resonator major surface and an opposing second resonator major surface, the resonator comprising a second magnetic material, the second resonator major surface facing toward the first magnetic surface, the first resonator major surface having a predefined channel,
- a spacer disposed between the magnetic bias layer and the resonator, and
- an environmental change receptor disposed proximate to the predefined channel.

2. The sensing device of claim 1, wherein the environmental change receptor distributes along at least part of the predefined channel in response to a change in environment.

3. The sensing device of claim 2, wherein resonant frequency of the resonator shifts in response to the distribution of the environmental change receptor along at least part of the predefined channel.

4. The sensing device of claim 1, wherein the predefined channel comprises a thin layer of material disposed on the first resonator major surface.

5. The sensing device of claim 4, wherein the thin layer of material comprises at least one of a hydrophilic material, a wicking material, a hydrophobic material, an oleophobic material, and an oleophilic material.

6. The sensing device of claim 4, wherein the thin layer of material has a chemical reaction with the second magnetic material.

7. The sensing device of claim 1, wherein the predefined channel comprises a pattern on the first resonator major surface.

8. The sensing device of claim 1, wherein the predefined channel comprises a thin layer of material disposed on the first resonator major surface according to a path.

9. The sensing device of claim 1, wherein the predefined channel comprises a thin layer of material disposed proximate to a perimeter of a path.

10. The sensor device of claim 1, wherein the predefined channel comprises an elongate channel across the first resonator major surface.

11. The sensing device of claim 1, wherein the predefined channel comprises one or more sections.

12. The sensing device of claim 11, wherein at least one of the one or more sections is disposed proximate an edge of the first resonator major surface.

13. The sensing device of claim 1, further comprising:
- a housing,
- wherein the magnetic bias layer, the resonator, and the spacer are disposed in the housing.

14. The sensing device of claim 13, wherein the housing comprising one or more openings to allow fluid distribution into the housing.

15. The sensing device of claim 13, wherein the housing has a plurality of chambers.

16. The sensing device of claim 15, wherein the magnetic bias layer and the resonator are disposed in a different chamber from each other.

17. The sensing device of claim 1, further comprising:
- a second resonator disposed adjacent to the magnetic bias layer.

18. A sensing device, comprising:
- a magnetic bias layer having a first magnetic surface and an opposing second magnetic surface, the magnetic bias layer comprising a first magnetic material,
- a resonator having a first resonator major surface and an opposing second resonator major surface, the resonator comprising a second magnetic material, the second resonator major surface facing toward the first magnetic surface, the first resonator major surface having a predefined channel,
- a spacer disposed between the magnetic bias layer and the resonator,
- an environmental change receptor disposed proximate to the predefined channel, and
- a housing with one or more openings, containing the magnetic bias layer, the resonator, and the spacer.

19. A sensing device, comprising:
- a magnetic bias layer having a first magnetic surface and an opposing second magnetic surface, the magnetic bias layer comprising a first magnetic material,
- a resonator having a first resonator major surface and an opposing second resonator major surface, the resonator comprising a second magnetic material, the second resonator major surface facing toward the first magnetic surface, the first resonator major surface having a predefined channel,
an environmental change receptor disposed proximate to the predefined channel, and
a housing containing the magnetic bias layer, the resonator, and a supporting structure to support the resonator.

20. The sensing device of claim 19, wherein the housing has a plurality of chambers.

* * * * *